US009827147B2

(12) United States Patent
Schneider et al.

(10) Patent No.: US 9,827,147 B2
(45) Date of Patent: *Nov. 28, 2017

(54) APPARATUSES AND METHODS FOR TRANSFERRING AND BONDING SUBSTRATES

(71) Applicant: The Procter & Gamble Company, Cincinnati, OH (US)

(72) Inventors: Uwe Schneider, Cincinnati, OH (US); Michael Devin Long, Springfield Township, OH (US); David C. Ordway, Oxford, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/005,381

(22) Filed: Jan. 25, 2016

(65) Prior Publication Data
US 2016/0220422 A1    Aug. 4, 2016

Related U.S. Application Data

(60) Provisional application No. 62/111,735, filed on Feb. 4, 2015.

(51) Int. Cl.
*B29C 65/00* (2006.01)
*A61F 13/15* (2006.01)
*B65H 35/08* (2006.01)

(52) U.S. Cl.
CPC .. *A61F 13/15699* (2013.01); *A61F 13/15739* (2013.01); *A61F 13/15804* (2013.01);
(Continued)

(58) Field of Classification Search
CPC .......... A61F 13/15699; A61F 13/15739; A61F 13/15764; A61F 13/15804;
(Continued)

(56) References Cited

U.S. PATENT DOCUMENTS 3,860,003 A    1/1975   Buell
4,610,678 A    9/1986   Weisman et al.
(Continued)

FOREIGN PATENT DOCUMENTS

EP    0 844 062 A1    5/1998

OTHER PUBLICATIONS

PCT International Search Report, dated May 20, 2016, 9 pages.
(Continued)

*Primary Examiner* — John Goff
(74) *Attorney, Agent, or Firm* — Sarah M. DeCristofaro

(57) ABSTRACT

A method and apparatus for mechanically deforming a substrate assembly. The substrate assembly may be advanced in a machine direction at a first velocity toward a bonder apparatus. The bonder apparatus may rotate about an axis of rotation and include a support surface between each of a first and a second member. The first member and the second member may be separated by a repitch angle. The second member may be repositioned such that the first member and the second member are separated by a product angle. The first member may receive a leading portion and second member may receive a trailing portion of the substrate assembly and each member may rotate at the first velocity. The leading portion and the trailing portion are separated by a product arc length, which may be equal to a process product pitch. The substrate assembly may then undergo one or more processes such as bonding, cutting, and/or scoring.

23 Claims, 13 Drawing Sheets

(52) U.S. Cl.
CPC .... *B65H 35/08* (2013.01); *A61F 2013/15715* (2013.01); *A61F 2013/15829* (2013.01); *A61F 2013/15861* (2013.01); *A61F 2013/15878* (2013.01); *B65H 2801/57* (2013.01)

(58) Field of Classification Search
CPC .. A61F 2013/15861; A61F 2013/15869; A61F 2013/15878; A61F 2013/15886; A61F 2013/15902; A61F 2013/1591; A61F 2013/15829; B29C 65/7847; B29C 65/7882; B29C 65/7885; B29C 66/3432; B29C 66/343; B29C 66/83411
USPC .................. 156/160, 163, 164, 229, 324
See application file for complete search history.

(56) References Cited

U.S. PATENT DOCUMENTS

| | | |
|---|---|---|
| 4,673,402 A | 6/1987 | Weisman et al. |
| 4,695,278 A | 9/1987 | Lawson |
| 4,704,115 A | 11/1987 | Buell |
| 4,795,454 A | 1/1989 | Dragoo |
| 4,834,735 A | 5/1989 | Alemany et al. |
| 4,888,231 A | 12/1989 | Angstadt |
| 4,909,803 A | 3/1990 | Aziz et al. |
| 5,562,646 A | 10/1996 | Goldman et al. |
| 5,599,335 A | 2/1997 | Goldman et al. |
| 5,628,097 A | 5/1997 | Benson et al. |
| 5,669,894 A | 9/1997 | Goldman et al. |
| 5,916,661 A | 6/1999 | Benson et al. |
| 6,107,539 A | 8/2000 | Palumbo et al. |
| 6,248,195 B1 | 6/2001 | Schmitz |
| 6,545,197 B1 | 4/2003 | Muller et al. |
| 6,790,798 B1 | 9/2004 | Suzuki et al. |
| 7,569,039 B2 | 8/2009 | Matsuda et al. |
| 7,587,966 B2 | 9/2009 | Nakakado et al. |
| 8,778,127 B2 | 7/2014 | Schneider et al. |
| 2002/0046802 A1* | 4/2002 | Tachibana .......... A61F 13/15593 156/209 |
| 2004/0089403 A1* | 5/2004 | Satoh ................. A61F 13/15593 156/160 |
| 2004/0097895 A1 | 5/2004 | Busam et al. |
| 2004/0158212 A1 | 8/2004 | Ponomarenko et al. |
| 2005/0107764 A1 | 5/2005 | Matsuda et al. |
| 2005/0241751 A1* | 11/2005 | Nakakado .......... A61F 13/15593 156/229 |
| 2009/0312730 A1 | 12/2009 | LaVon et al. |
| 2012/0061015 A1 | 3/2012 | LaVon et al. |
| 2012/0061016 A1 | 3/2012 | LaVon et al. |
| 2013/0213547 A1* | 8/2013 | Schneider ............ A61F 13/4963 156/60 |
| 2013/0218116 A1 | 8/2013 | Schneider et al. |
| 2013/0255861 A1 | 10/2013 | Schneider |
| 2013/0255862 A1 | 10/2013 | Schneider et al. |
| 2013/0255863 A1 | 10/2013 | LaVon et al. |
| 2013/0255864 A1 | 10/2013 | Schneider et al. |
| 2013/0255865 A1 | 10/2013 | Brown et al. |
| 2014/0000798 A1 | 1/2014 | Hargett et al. |
| 2014/0110053 A1 | 4/2014 | Ordway et al. |
| 2014/0305593 A1 | 10/2014 | Schneider et al. |
| 2015/0202727 A1 | 7/2015 | Yamamoto et al. |

OTHER PUBLICATIONS

PCT international Search Report, dated May 4, 2016, 10 pages.
U.S. Appl. No. 15/005,398, filed Jan. 25, 2016, Schneider, et al.
U.S. Appl. No. 15/005,413, filed Jan. 25, 2016, Schneider, et al.

* cited by examiner

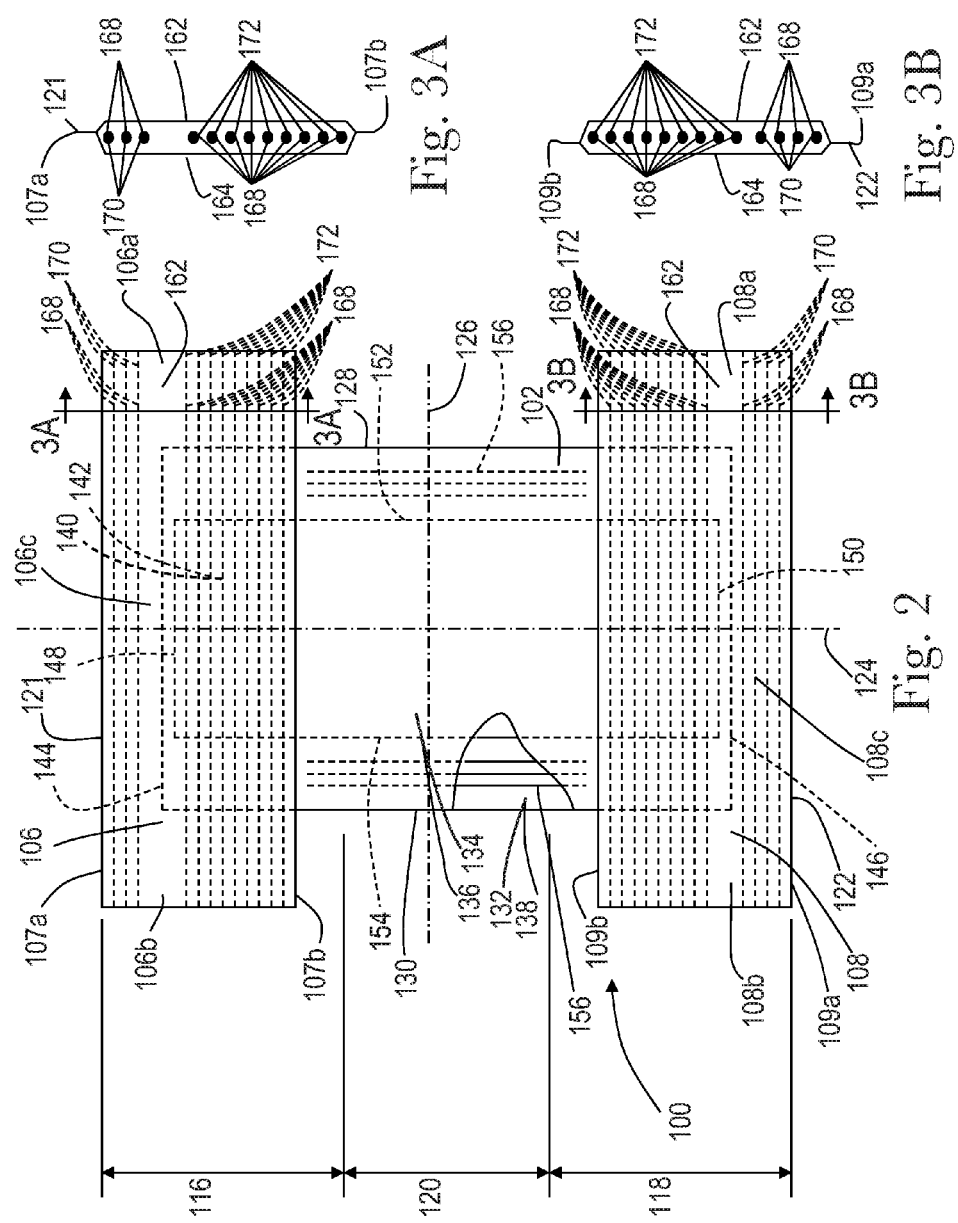

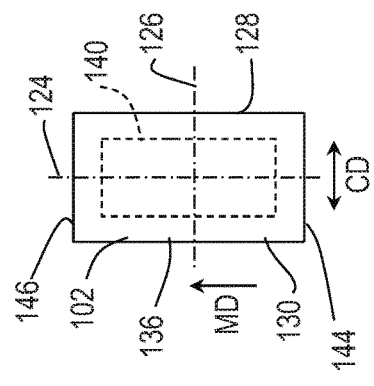
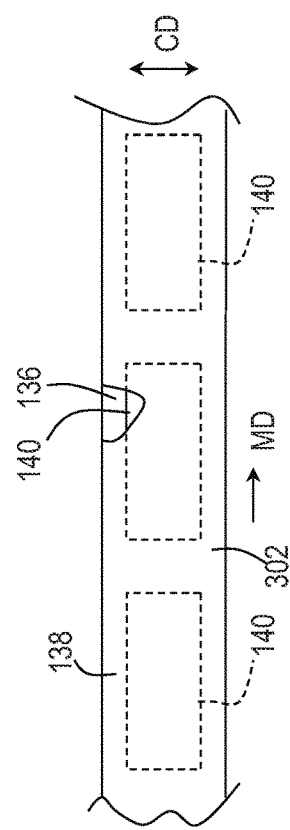
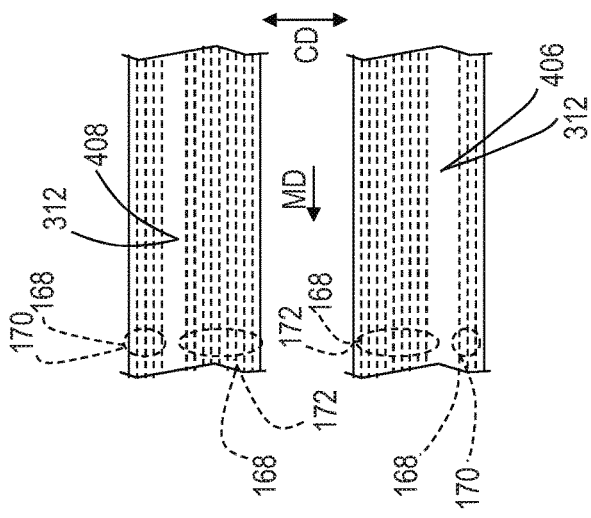

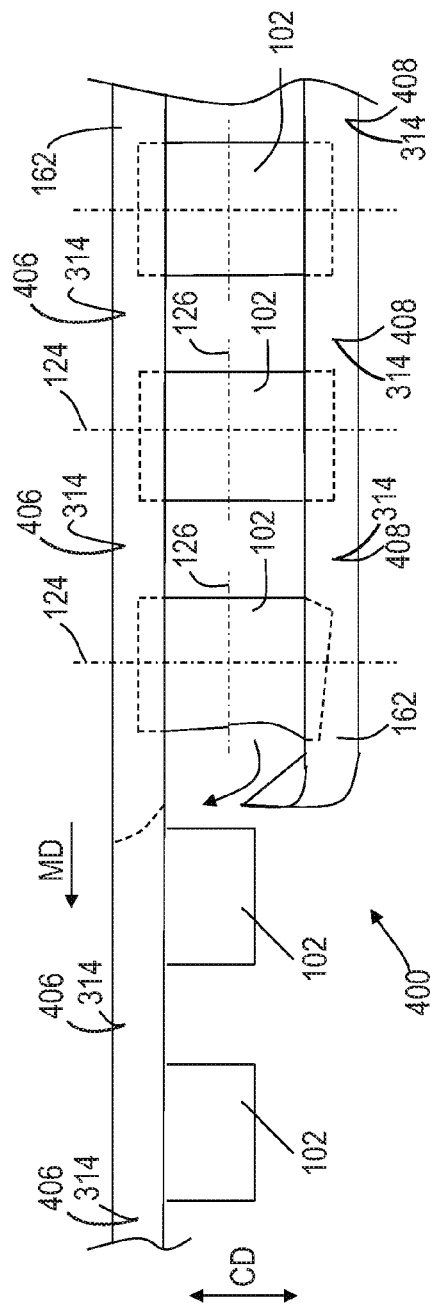
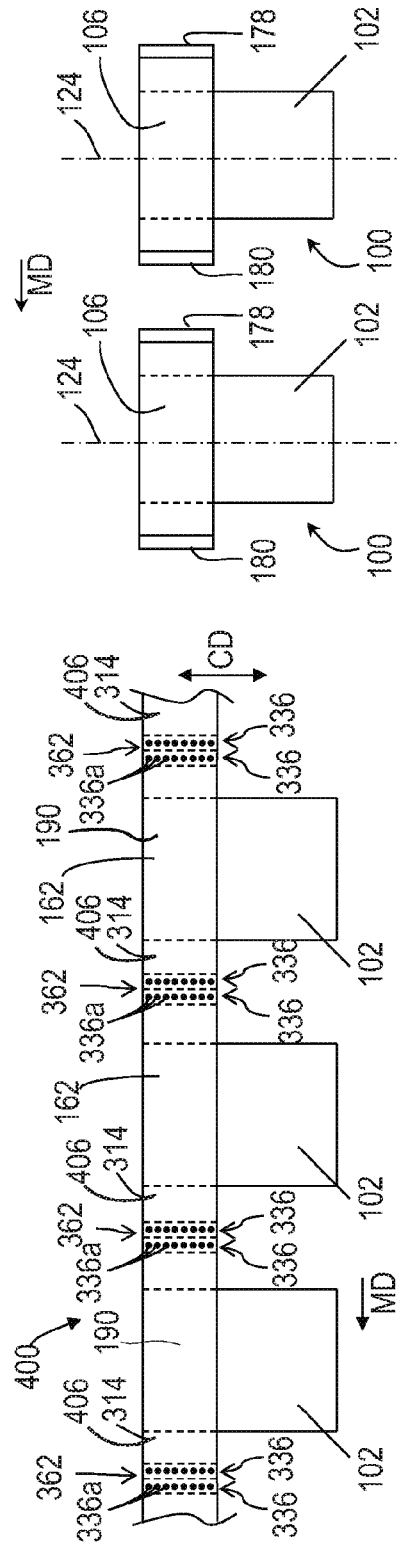

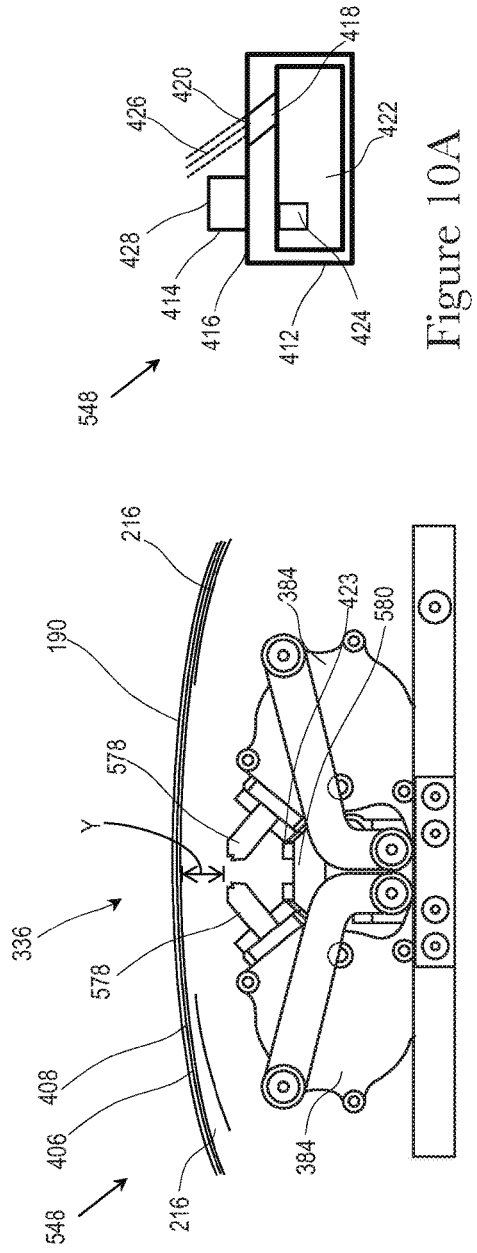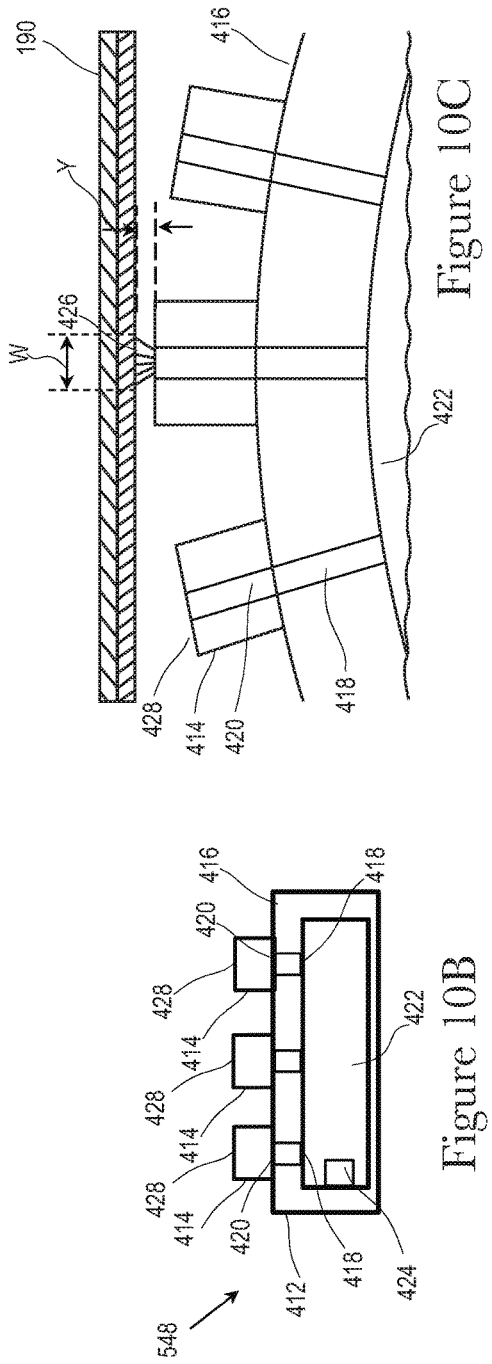

APPARATUSES AND METHODS FOR TRANSFERRING AND BONDING SUBSTRATES

CROSS REFERENCE TO RELATED APPLICATIONS

This application claims the benefit of U.S. Provisional Application No. 62/111,735 filed on Feb. 4, 2015, which is herein incorporated herein by reference.

TECHNICAL FIELD

The present disclosure relates to methods for manufacturing absorbent articles, and more particularly, to apparatuses and methods for bonding two or more partially meltable materials.

BACKGROUND

Disposable absorbent articles, in particular, disposable diapers, are designed to be worn by people experiencing incontinence, including infants and invalids. Such diapers are worn about the lower torso of the wearer and are intended to absorb and contain urine and other bodily discharges, thus preventing the soiling, wetting, or similar contamination of articles that may come into contact with a diaper during use (e.g., clothing, bedding, other people, etc.). Disposable diapers are available in the form of pull-on diapers, also referred to as training pants, having fixed sides, or taped diapers having unfixed sides.

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web or webs are combined with other individual components created from other advancing web or webs.

Webs of material and component parts used to manufacture diapers may include: backsheets, topsheets, leg cuffs, waist bands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some converting configurations, discrete chassis spaced apart from each other are advanced in a machine direction and are arranged with a longitudinal axis parallel with the cross direction. Opposing waist regions of discrete chassis are then connected with continuous lengths of elastically extendable front and back belt webs advancing in the machine direction. While connected with the chassis, the front and back belt webs are maintained in a fully stretched condition along the machine direction, forming a continuous length of absorbent articles. The continuous length of absorbent articles may then be folded in a cross direction. During the folding process in some converting configurations, one of the front and back belt webs is folded into a facing relationship with the opposing belt. The front and back belts may then be bonded together to create the side seams on diapers.

Diapers come in a variety of sizes. Thus, one diaper may include a larger chassis and a larger belt as compared to another diaper which may include a smaller chassis and a smaller belt. The manufacturing process for these absorbent articles is desired to be such that the diaper including the larger chassis and the larger belt can be manufactured on the same equipment or similar equipment as the diaper including the smaller chassis and the smaller belt. Having to switch out equipment or to make large modifications to the equipment for manufacturing different sized articles is costly and time consuming for manufacturers.

Thus, it would be beneficial to provide an apparatus and a method for transferring and bonding absorbent articles of different sizes.

SUMMARY

Aspects of the present disclosure involve apparatuses and methods for manufacturing absorbent articles, and more particularly, methods for mechanically deforming substrates during the manufacture of disposable absorbent articles. Particular embodiments of methods of manufacture disclosed herein provide for forming side seams in various types of diaper configurations. It is to be appreciated that the methods and apparatuses disclosed herein can also be applied to other seams or other forms of mechanical deformation used on diapers as well as other types of absorbent articles.

In one embodiment, a method for transferring and bonding includes the steps of: advancing a substrate assembly in a machine direction at a first velocity, wherein the substrate assembly comprises a process product pitch defined by a leading portion and a trailing portion, and wherein the substrate assembly comprises a first substrate in facing relationship with a second substrate; rotating a bonder apparatus about an axis of rotation, wherein the bonder apparatus comprises a support surface between each of a first member and a second member adjacent the first member, wherein each of the first and second member comprises a proximal end portion adjacent the axis of rotation and a distal end portion opposite the proximal end portion; rotating the first member about the axis of rotation at the first velocity, wherein the first member comprises a first receiving surface positioned at the distal end portion of the first member; receiving the leading portion on the first receiving surface of the first member, wherein the first member and the second member are separated by a repitch angle; at least one of accelerating and decelerating the second member such that the first member and the second member are separated by a product angle, wherein the second member comprises a second receiving surface positioned at the distal end portion of the second member; receiving the first trailing portion on the second receiving surface of the second member and rotating the second member about the axis of rotation at the first velocity, wherein the leading portion and the first trailing portion are separated by a product arc length, wherein the product arc length is substantially equal to the process product pitch; heating a fluid to a temperature sufficient to at least partially melt the first substrate and the second substrate; directing a jet of the fluid toward at least one of the leading portion and the first trailing portion; partially melting at least a portion of at least one of the leading portion and the first trailing portion; and compressing a portion of the substrate assembly.

In another embodiment, a method for forming a bond, the method comprising the steps of: advancing a substrate assembly in a machine direction at a first velocity, wherein the substrate assembly comprises a process product pitch defined by a leading portion and a trailing portion; rotating a bonder apparatus about an axis of rotation, wherein the bonder apparatus comprises a support surface between each of a first member and a second member adjacent the first member, wherein each of the first and second member comprises a proximal end portion adjacent the axis of rotation and a distal end portion opposite the proximal end portion, and wherein the bonder apparatus comprises a process zone and a repitch zone; rotating the first member and the second member about the axis of rotation at the first velocity in the process zone, wherein the first member comprises a first receiving surface positioned at the distal end portion of the first member and second member comprises a second receiving surface positioned at the distal end portion of the second member; transferring the leading portion on the first receiving surface and transferring the first trailing portion on the second receiving surface in the process zone, wherein the first receiving surface and the second receiving surface are positioned such that the leading portion and the first trailing portion are separated by a product arc length; heating a fluid to a temperature sufficient to at least partially melt a portion of the substrate assembly; directing a j et of the heated fluid toward the substrate assembly; partially melting a portion of the substrate assembly; and at least one of accelerating and decelerating the first member and the second member in the repitch zone, wherein the substrate assembly is not disposed on first receiving surface and the second receiving surface.

In another embodiment, an apparatus for bonding a substrate assembly together may comprise a shaft member defining an axis of rotation. The shaft member may extend in a cross direction. The apparatus may also include a first member and a second member. The first member may include a proximal end portion and a distal end portion opposite the proximal end portion. The proximal end portion may be rotatably connected to the shaft member. The second member may include a proximal end portion and a distal end portion opposite the proximal end portion, and the proximal end portion may be rotatably connected to the shaft member. A first receiving surface may be positioned at the distal end portion of the first member. The first receiving surface may extend in a direction substantially parallel to the shaft member, and the first receiving surface may define one or more apertures configured to aid in at least one of holding and removing a substrate assembly from the first receiving surface. A second receiving surface may be positioned at the distal end portion of the second member. The second receiving surface may extend in a direction substantially parallel to the shaft member, and the second receiving surface may define one or more apertures configured to aid in at least one of holding and removing the substrate assembly from the second receiving surface. A support surface may extend between the first member and the second member. The support surface may include a first support segment and a second support segment. Each of the first support segment and the second support segment may include a distal end portion and a proximal end portion opposite the distal end portion. The proximal end portion of the first support segment may extend from to the first receiving surface and the proximal end portion of the second support segment may extend from the second receiving surface. The distal end portion of the first support segment may be configured to operatively engage the distal end portion of the second support segment. A process assembly may be positioned adjacent the receiving surface. The process assembly may include a seaming station. The seaming station may include a fluid nozzle positioned adjacent to the substrate assembly, and the fluid nozzle may be adapted to direct a fluid radially outward toward the substrate assembly. The fluid may be configured to partially melt at least a portion of the substrate assembly.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 2 is a partially cut away plan view of the diaper pant shown in FIG. 1;

FIG. 3A is a cross-sectional view of the diaper pant of FIG. 2 taken along line 3A-3A of FIG. 2;

FIG. 3B is a cross-sectional view of the diaper pant of FIG. 2 taken along line 3B-3B of FIG. 2;

FIG. 5A is a top view of a chassis assembly taken along line 5A-5A of FIG. 4 in accordance with one non-limiting embodiment of the present disclosure;

FIG. 5B1 is a top view of a discrete chassis taken along line 5B1-5B1 of FIG. 4 in accordance with one non-limiting embodiment of the present disclosure;

FIG. 5B2 is a top view of a discrete chassis taken along line 5B2-5B2 of FIG. 4 in accordance with one non-limiting embodiment of the present disclosure;

FIG. 5C is a top view of elastic belt substrates taken along line 5C-5C of FIG. 4 in accordance with one non-limiting embodiment of the present disclosure;

FIG. 5D is a top view of multiple discrete chassis attached to a first elastic belt substrate and a second elastic belt substrate taken along line 5D-5D of FIG. 4 in accordance with one non-limiting embodiment of the present disclosure;

FIG. 5E is a top view of multiple discrete chassis attached to a substrate assembly taken along line 5E-5E of FIG. 4 in accordance with one non-limiting embodiment of the present disclosure;

FIG. 5F is a top view of two discrete absorbent articles taken along line 5F-5F of FIG. 4 in accordance with one non-limiting embodiment of the present disclosure;

FIG. 9 is a side view of a seaming station in accordance with one non-limiting embodiment of the present disclosure;

FIG. 10A is a side view of a seaming station in accordance with one non-limiting embodiment of the present disclosure;

FIG. 10B is a side view of a seaming station in accordance with one non-limiting embodiment of the present disclosure;

FIG. 10C is a partial side view of a seaming station in accordance with one non-limiting embodiment of the present disclosure;

DETAILED DESCRIPTION

Figure 1:
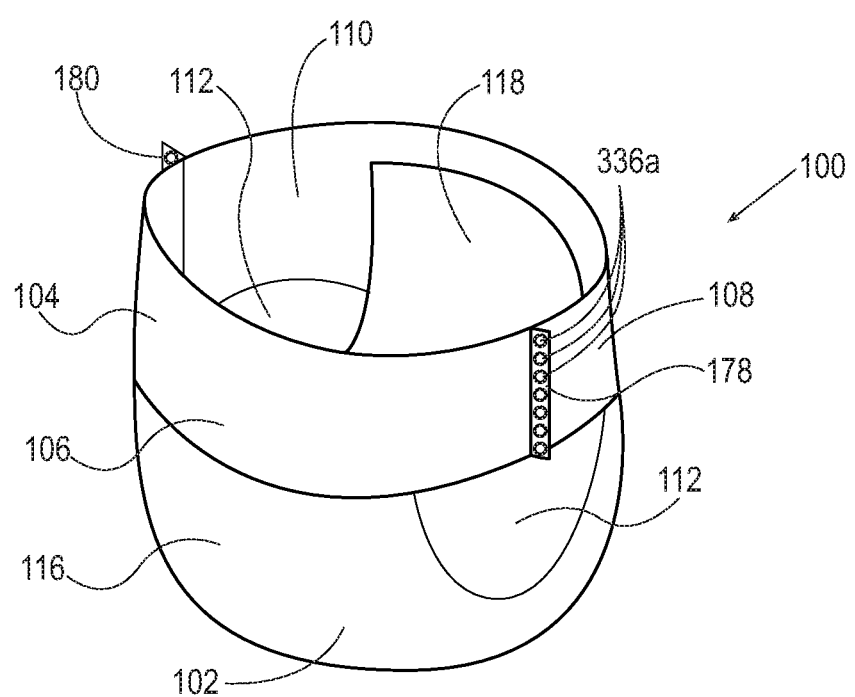
FIG. 1 is a perspective view of a diaper pant.

The methods and apparatuses described herein relate to transferring and bonding substrates. In general, portions of substrates may be overlapped and a jet of heated fluid is delivered from an orifice to at least partially melt the overlapping substrate portions. More particularly, the jet of heated fluid penetrates the substrate portions and at least partially melts the overlapping substrate portions where the substrate portions interface at an overlap area. The location of the substrate portions relative to the orifice may be controlled such that the substrate portions are held a predetermined distance away from the orifice during the heating operation. Pressure may then be applied at the overlap area thereby joining the substrate portions together. In all the embodiments described herein, the fluid may include ambient air or other gases.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

As used herein, the term "joining" describes a configuration whereby a first element is directly secured to another element by affixing the first element directly to the other element.

As used herein, the term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a substrate, layer or layers or fibrous materials, nonwovens, films and foils such as polymeric films or metallic foils. These materials may be used alone or may comprise two or more layers laminated together. As such, a web is a substrate.

As used herein, the term "pull-on diaper" refers to a garment that is generally worn by infants and sufferers of incontinence, which is pulled on like pants. It should be understood, however, that the present disclosure is also applicable to other absorbent articles, such as taped diapers, incontinence briefs, feminine hygiene garments, and the like, including absorbent articles intended for use by infants, children, and adults.

As used herein, the term "at least partially melted" refers to materials at least a portion of which have reached at least a softening point temperature, but have not reached a melt point temperature. "Melted" also refers, in its ordinary sense, to materials which have exceeded their melt point temperatures over at least a portion of the material. "Meltable" refers to materials that at least soften when heated or when some other energy is applied or generated.

The present disclosure relates to methods and apparatuses for bonding substrates together. As discussed in more detail below, the bonder apparatus is rotated about an axis of rotation and a substrate assembly may be advanced in a machine direction and received on the bonder apparatus. The bonder apparatus may adjust the velocity of the substrate assembly prior to bonding. A portion of the substrate assembly may undergo bonding by a seaming station as the substrate assembly continues to rotate with the bonder apparatus. Further, in some embodiments, the substrate assembly may be compressed.

As discussed below, the bonder apparatus may be configured to partially melt and/or compress the substrates while traveling on the bonder apparatus to minimize deformation of weak, partially melted substrates as the substrates advance in the machine direction MD. More specifically, a fluid is heated to a temperature sufficient to at least partially melt a portion of the substrate assembly. As the bonder apparatus rotates, the fluid nozzle moves radially outward toward the aperture in the outer circumferential surface of the drum. The fluid nozzle directs a jet of the heated fluid through the aperture and onto an area of the substrate assembly, which partially melts the area. As the bonder apparatus continues to rotate, the fluid nozzle retracts radially inward from the aperture, and the press member moves radially outward through the aperture. The partially melted area is then compressed between a press member and an anvil roll or anvil block, creating a discrete bond region or seam. The bonder apparatus continues to rotate and the press member retracts radially inward from the aperture. In some embodiments, the operative connection between the fluid nozzle and the press member may be configured to partially melt and compress the substrates at the same relative location in order to create a bond.

As described in greater detail below, a seam may be formed between at least two substrate layers, each substrate layer comprising one or more meltable components. A seam may also be formed between portions of the same substrate that is, for example, folded along a fold line formed between two substrate portions. The substrate portions to be bonded may be positioned adjacent one another.

It is to be appreciated that although the transfer and bonding methods and apparatuses herein may be configured to bond various types of substrates, the methods and apparatuses herein are discussed below in the context of manufacturing absorbent articles. In particular, the methods and apparatuses are discussed in the context of bonding substrates, such as belts, together to form side seams of advancing, continuous lengths of absorbent articles during production. As discussed below, an advancing continuous length of absorbent articles may include a plurality of chassis connected with a continuous first substrate and a continuous second substrate.

The continuous first and second substrates may be separated from each other along a cross direction while advancing along a machine direction MD. Each chassis may extend in the cross direction CD and may include opposing first and second end regions separated by a central region, wherein the first end regions are connected with the first substrate and the second end regions are connected with the second substrate. The chassis may also be spaced from each other along the machine direction MD. A folding apparatus operates to fold the chassis around the folding axis along the central regions and to bring the second substrate and second end region of the chassis into a facing relationship with the first substrate and first end region of the chassis. The first substrate and the second substrate in a facing relationship form a substrate assembly. The substrate assembly and the folded chassis advance in the machine direction onto the bonder apparatus such as described above.

The methods and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

FIGS. 1 and 2 show an example of a diaper pant 100 that may be transferred and/or bonded with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also comprise a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also comprise an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

As previously mentioned, the diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730 A1; and U.S. Patent Publication No. 2013/0255865 A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140.

In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to transfer and/or bond discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. 2005/0107764 A1, 2012/0061016 A1, and 2012/0061015 A1; 2013/0255861 A1; 2013/0255862 A1; 2013/0255863 A1; 2013/0255864 A1; and 2013/0255865 A1.

Figure 4:
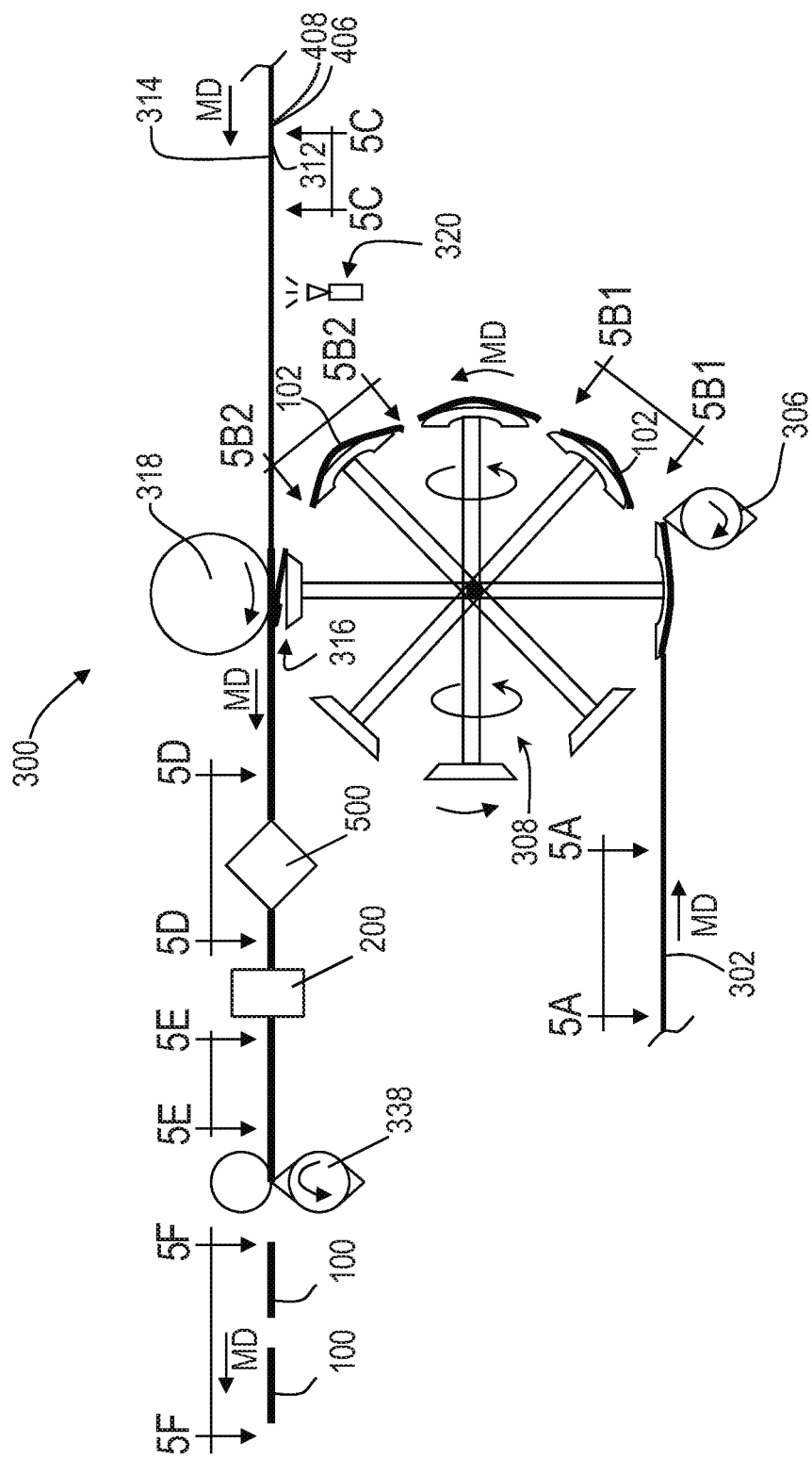
FIG. 4 is a schematic representation of a converting apparatus in accordance with one non-limiting embodiment of the present disclosure.

As previously mentioned, the apparatuses and methods according to the present disclosure may be utilized to assemble various components of absorbent articles 100. For example, FIG. 4 shows a schematic view of a converting apparatus 300 adapted to manufacture absorbent articles 100. The method of operation of the converting apparatus 300 may be described with reference to the various components of absorbent articles 100, such as described above and shown in FIGS. 1 and 2. Although the following methods are provided in the context of the absorbent article 100 shown in FIGS. 1 and 2, it is to be appreciated that various embodiments of diaper pants can be manufactured according to the methods disclosed herein, such as for example, the absorbent articles disclosed in U.S. Pat. No. 7,569,039 and U.S. Patent Publication Nos. 2005/0107764A1; 2012/0061016A1; and 2012/0061015A1.

As described in more detail below, the converting apparatus 300 shown in FIG. 4 operates to advance discrete chassis 102 along a machine direction MD such that the lateral axis of each chassis 102 is parallel with the machine direction, and wherein the chassis 102 are spaced apart from each other along the machine direction. Opposing waist regions 116, 118 of the spaced apart chassis 102 are then connected with continuous lengths of advancing first and second elastic substrates 406, 408. The chassis 102 are then folded along the lateral axis to bring the first and second elastic substrates 406, 408 into a facing relationship, and the first and second elastic substrates are connected together along regions 336 intermittently spaced along the machine direction, wherein each region 336 may include one or more discrete bond sites 336a. And the elastic substrates 406, 408 are cut along the regions 336 to form a discrete belt and creating discrete absorbent articles 100, such as shown in FIG. 1.

As shown in FIGS. 4 and 5A, a continuous length of chassis assemblies 302 are advanced in a machine direction MD to a carrier apparatus 308 and cut into discrete chassis 102 with knife roll 306. The continuous length of chassis assemblies 302 may include absorbent assemblies 140 sandwiched between topsheet material 138 and backsheet material 136, leg elastics, barrier leg cuffs and the like. A portion of the chassis assembly is cut-away to show a portion of the backsheet material 136 and an absorbent assembly 140.

After the discrete absorbent chassis 102 are cut by the knife roll 306, the carrier apparatus 308 rotates and advances the discrete chassis 102 in the machine direction MD in the orientation shown in FIG. 5B1, wherein the longitudinal axis 124 of the chassis 102 is generally parallel with the machine direction MD. While the chassis 102 shown in FIG. 5B1 is shown with the second laterally extending end edge 146 as a leading edge and the first laterally extending end edge 144 as the trailing edge, it is to be appreciated that in other embodiments, the chassis 102 may be advanced in other orientations. For example, the chassis may be oriented such that the second laterally extending end edge 146 is a trailing edge and the first laterally extending end edge 144 is a leading edge. The carrier apparatus 308 also rotates while at the same time changing the orientation of the advancing chassis 102. The carrier apparatus 308 may also change the speed at which the chassis 102 advances in the machine direction MD. It is to be appreciated that various forms of carrier apparatuses may be used with the methods herein, such as for example, the carrier apparatuses disclosed in U.S. Pat. No. 7,587,966. FIG. 5B2 shows the orientation of the chassis 102 on the carrier apparatus 308 while advancing in the machine direction. More particularly, FIG. 5B2 shows the chassis 102 with the lateral axis 126 of the chassis 102 generally parallel with the machine direction MD, and wherein the second longitudinal side edge 130 is the leading edge and the first longitudinal side edge 128 is the trailing edge.

As discussed below with reference to FIGS. 3, 5C, 5D, 5E, and 5F, the chassis 102 are transferred from the carrier apparatus 308 and combined with advancing, continuous lengths of belt substrates 406, 408, which are subsequently cut to form first and second elastic belts 106, 108 on diapers 100.

With reference to FIG. 4, the chassis 102 are transferred from the carrier apparatus 308 to a nip 316 between the carrier apparatus 308 and a carrier apparatus 318 where the chassis 102 is combined with continuous lengths of advancing first elastic belt substrate 406 and second elastic belt substrate 408. The first substrate material 406 and the second substrate material 408 each define a wearer facing surface 312 and an opposing garment facing surface 314, as illustrated in FIG. 5C. The wearer facing surface 312 of the first substrate 406 may be combined with the garment facing surface 134 of the chassis 102 along the first waist region 116, and the wearer facing surface 312 of the second substrate 408 may be combined with the garment facing surface 134 of the chassis 102 along the second waist region 118. As shown in FIG. 4, adhesive 320 may be intermittently applied to the wearer facing surface 312 of the first and second substrates 406, 408 before combining with the discrete chassis 102 at the nip 316 between roll 318 and the carrier apparatus 308.

With reference to FIGS. 4 and 5D, a continuous length of absorbent articles 400 are defined by multiple discrete chassis 102 spaced from each other along the machine direction MD and connected with each other by the substrate assembly 190 which includes the second substrate 408 and the first substrate 406. As shown in FIG. 4, the continuous length of absorbent articles 400 advances from the nip 316 to a folding apparatus 500. At the folding apparatus 500, each chassis 102 is folded in the cross direction CD along a lateral axis 126 to place the first waist region 116, and specifically, the inner, body facing surface 132 into a facing, surface to surface orientation with the inner, body surface 132 of the second waist region 118. The folding of the chassis also positions the wearer facing surface 312 of the second belt substrate 408 extending between each chassis 102 in a facing relationship with the wearer facing surface 312 of the first belt substrate 406 extending between each chassis 102. As shown in FIGS. 4, 5D, and 5E, the folded discrete chassis 102 connected with the first and second substrates 406, 408 are advanced from the folding apparatus 500 to a bonder apparatus 200. The bonder apparatus 200 operates to bond, at least a portion of the region 336, which may include an overlap area 362, of the substrate assembly 190 thus creating discrete bond sites 336a. An overlap area 362 includes a portion of the second substrate 408 extending between each chassis 102 and a portion of the first substrate 406 extending between each chassis 102. As shown in FIGS. 4 and 5F, a continuous length of absorbent articles are advanced from the bonder apparatus 200 to a knife roll 338 where the regions 336 are cut into along the cross direction to create a first side seam 178 and a second side seam 180 on an absorbent article 100.

Although the absorbent article is described as having a substrate assembly that includes first and second substrates, it is to be appreciated that the absorbent article may have only one substrate or, alternatively, one or more substrates. For example, the substrate assembly may include a first substrate, a second substrate, a third substrate, and a fourth substrate. Further, it is to be appreciated that the chassis and substrate of the absorbent article may be one continuous substrate such that the overlap area is formed from the same substrate. As such, the bonder apparatus may operate to bond a continuous substrate at an overlap area to form one or more discrete bond sites.

Figure 6:
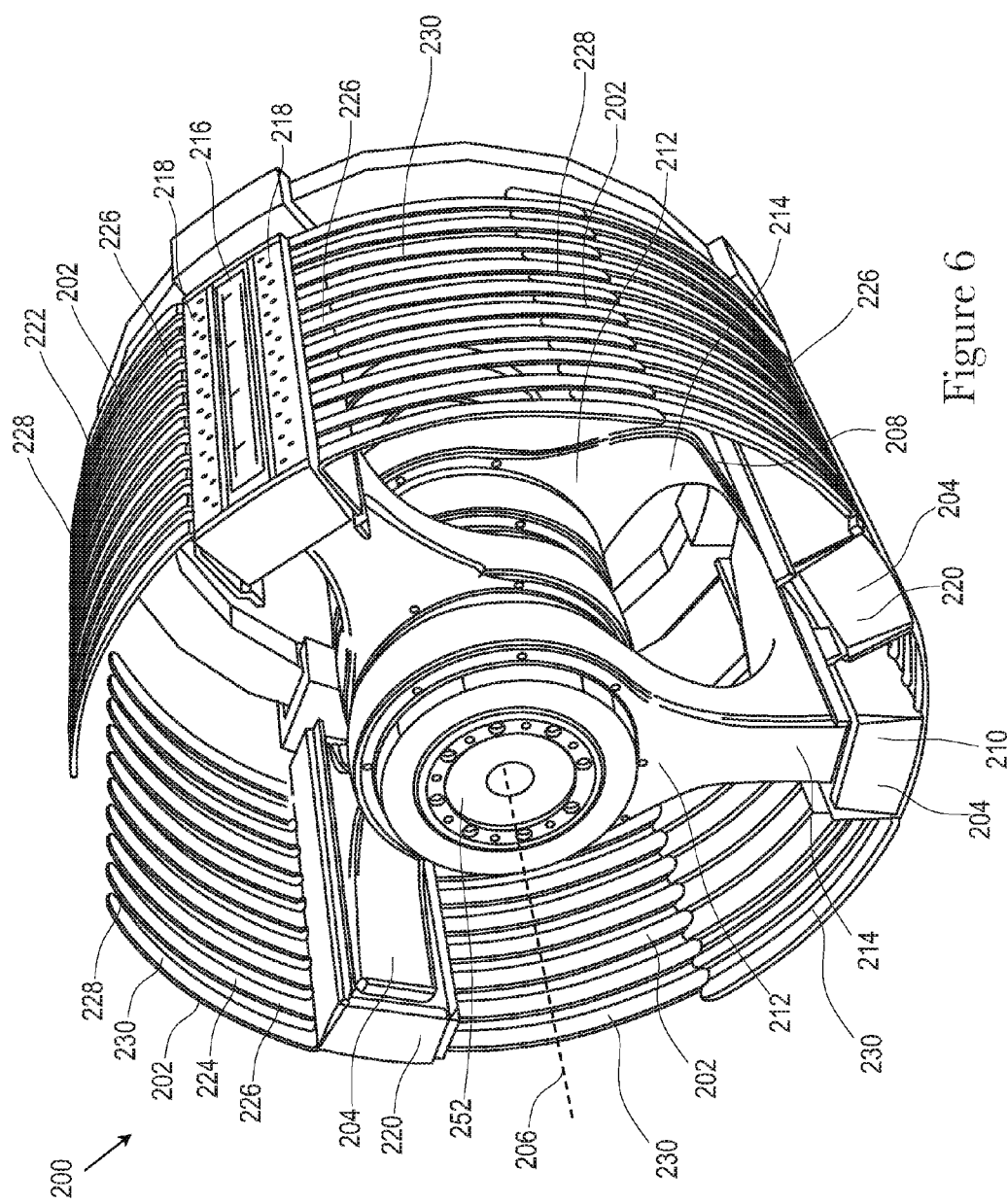
FIG. 6 is a perspective view of a bonder apparatus in accordance with one non-limiting embodiment of the present disclosure.

As previously discussed, the converting apparatus 300 may include a bonder apparatus 200. For example, FIG. 6 illustrates a perspective view of an embodiment of a bonder apparatus 200 that may be used with the methods and apparatuses herein. As shown in FIG. 6, the bonder apparatus 200 may include a shaft 252 rotatable about an axis of rotation 206. Further, the bonder apparatus 200 may include a support surface 202 and two or more members 204. The two or more members 204 and the support surface 202 may be adapted to rotate about an axis of rotation 206. For example, in some embodiments, the bonder apparatus 200 may include a first member 208 and a second member 210, adjacent the first member 208. Each of the first member 208 and the second member 210 may be adapted to rotate about the axis of rotation 206. Each of the first member 208 and the second member 210 may include a proximal end portion 212 adjacent to the axis of rotation 206 and a distal end portion 214 opposite the proximal end portion 212. The proximal end portion of each of the first member and the second member may be rotatably connected to the shaft member 252. Each member may be driven by a motor. The motor may be any device that transmits rotational energy to the member. The motor may be operatively linked or operatively engaged with the member using any technique known to those skilled in the art such as, for example, a gear to gear connection, transmission belting and pulleys, gearboxes, direct couplings, and the like or any combination thereof.

The bonder apparatus may also include a receiving surface 216. The receiving surface 216 may be positioned at the distal end portion 214 of each of the members. The receiving surface 216 may be configured to receive a portion of the substrate assembly, which will be discussed in more detail herein. The receiving surface 216 may include one or more apertures 218, also referred herein as fluid apertures and vacuum apertures. The apertures 218 may be used to control the position of the substrate assembly. For example, the one or more apertures 218 may be used to transfer fluid, such as air, through the one or more apertures in a direction toward the axis of rotation 206 causing the substrate assembly to be held against the receiving surface 216, which forms a vacuum force. The one or more apertures 218 may also be used to transfer fluid, such as air, through the one or more apertures in a direction away from the axis of rotation 206 causing the substrate assembly to be forced away from the receiving surface 216, which forms a pressure force. In some embodiments, the apertures 218 may be configured to supply a vacuum force on the substrate assembly and other apertures 218 may be configured to supply a pressure force on the substrate assembly. However, it is to be appreciated that the same aperture 218 may be used to supply both a vacuum force and a pressure force on at least a portion of the substrate assembly.

In some embodiments, the bonder apparatus 200 may also include a process assembly 220. The process assembly 220 may be positioned adjacent the receiving surface 216. The process assembly 220 may be used, for example, to bond the substrate assembly and/or cut the substrate assembly, and/or to alter in some other manner the substrate assembly. The process assembly 220 will be described in more detail herein. It is to be appreciated that the receiving surface 216 may be part of the process assembly 220, or the receiving surface 216 may be a separate component from the process assembly 220.

Still referring to FIG. 6, the support surface 202 may include one or more support segments. For example, the support surface 202 may include a first support segment 222 and a second support segment 224. Each of the first support segment 222 and the second support segment 224 may include a proximal end portion 226 adjacent the member 204 and a distal end portion 228 opposite the proximal end portion 226. The proximal end portion 226 of a support segment may be attached to a portion of at least one of a member 204, a process assembly 220, and a receiving surface 216. The distal end portion 228 of the support segment extends in a direction away from the member 204 and toward a distal end portion 228 of an adjacent support segment. More specifically, for example, the proximal end portion 226 of a first support segment 222 and a proximal end portion 226 of a second support segment 224 may each extend from a portion of the support surface. The proximal end portion 226 of the first support segment 222 may extend from a support surface 202 disposed on a first member 208 and the proximal end portion 226 of the second support segment 224 may extend from a support surface 202 disposed on a second member 210. As the first member 208 and the second member 210 rotate about the axis of rotation 206, the distance between the first member and the second member changes. Thus, the first support segment 222 and the second support segment 224 may operatively engage to allow the distance between the first member 208 and the second member 210 to increase and decrease.

Figure 8A:
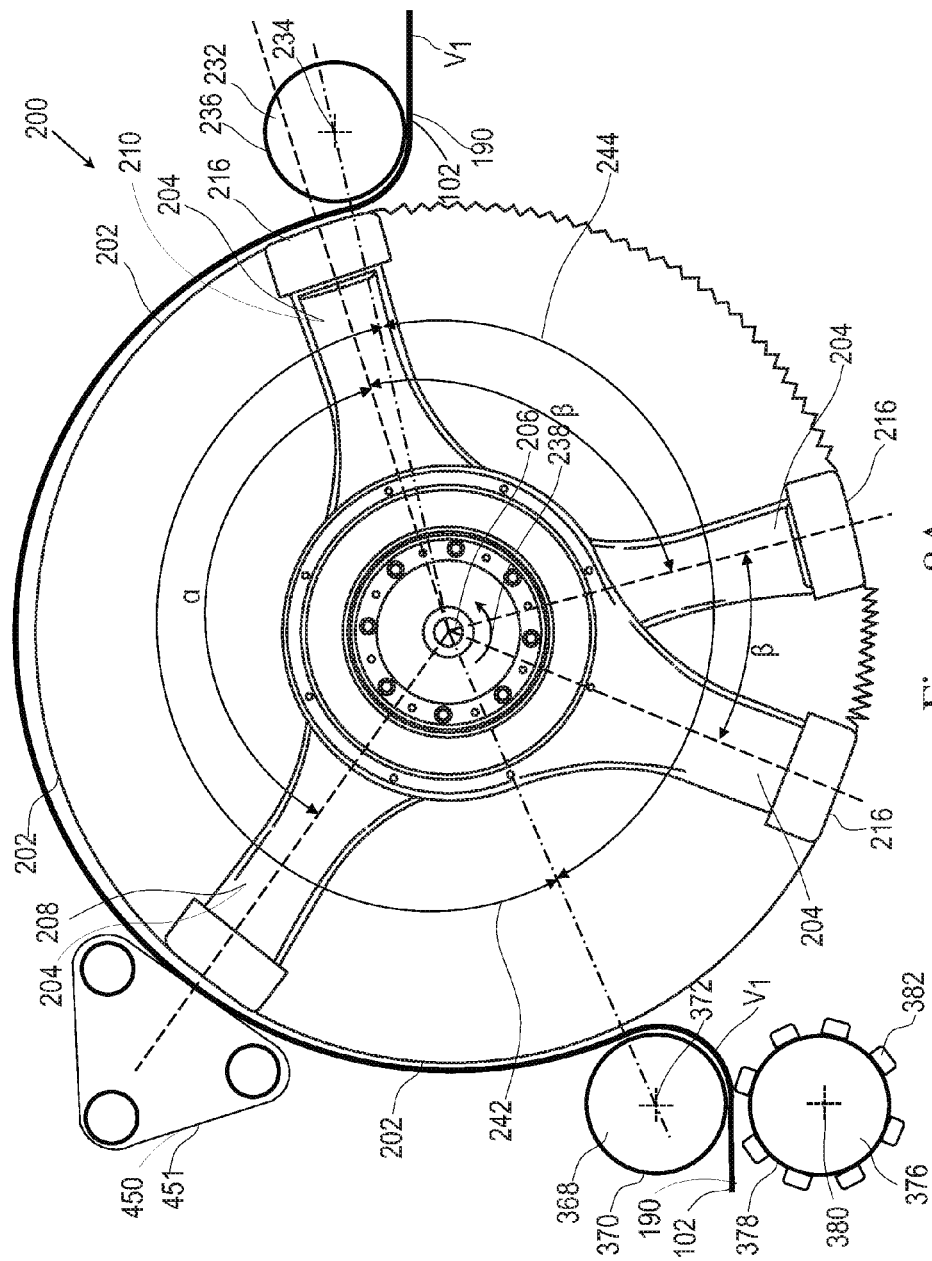
FIG. 8A is a side view of a bonder apparatus in accordance with one non-limiting embodiment of the present disclosure.

In one embodiment, each of the first support segment 222 and the second support segment 224 may include one or more protrusions 230. The protrusions 230 of the first support segment 222 may be configured to intermesh with the protrusions 230 of the second support segment 224, as illustrated in FIG. 6. Further, the protrusions 230 may be configured to overlap a portion of the receiving surface 216, as illustrated in FIG. 6. In some embodiments, each of the first support segment 222 and the second support segment 224 may include a collapsible surface, such as a surface including a tooth-like design, as shown in FIG. 8A. It is to be appreciated that each support segment may be any structure that is configured to create a variable arc length, which allows the distance or angle between adjacent members to change.

Figure 7:
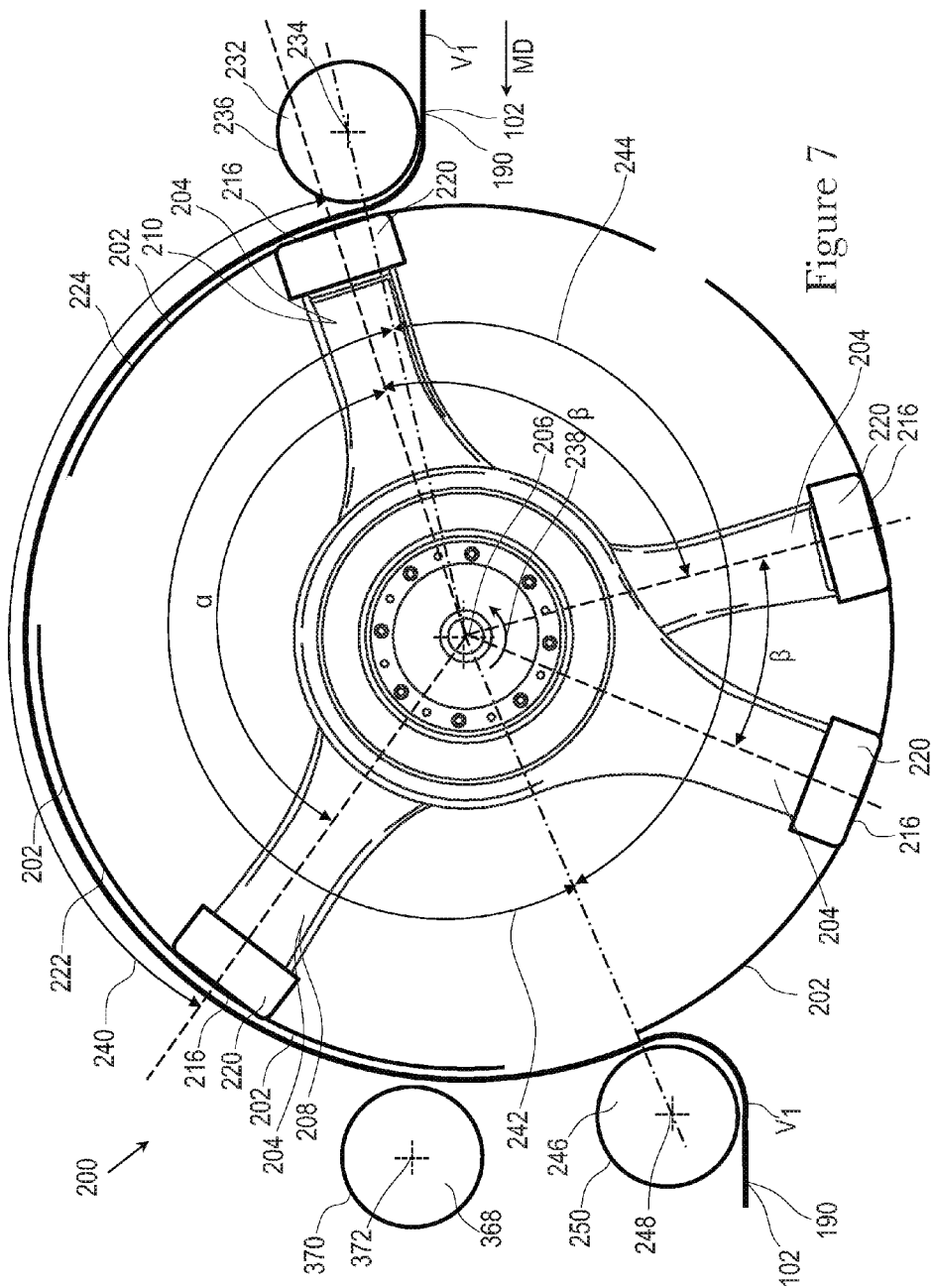
FIG. 7 is a side view of a bonder apparatus in accordance with one non-limiting embodiment of the present disclosure.
Figure 7A:
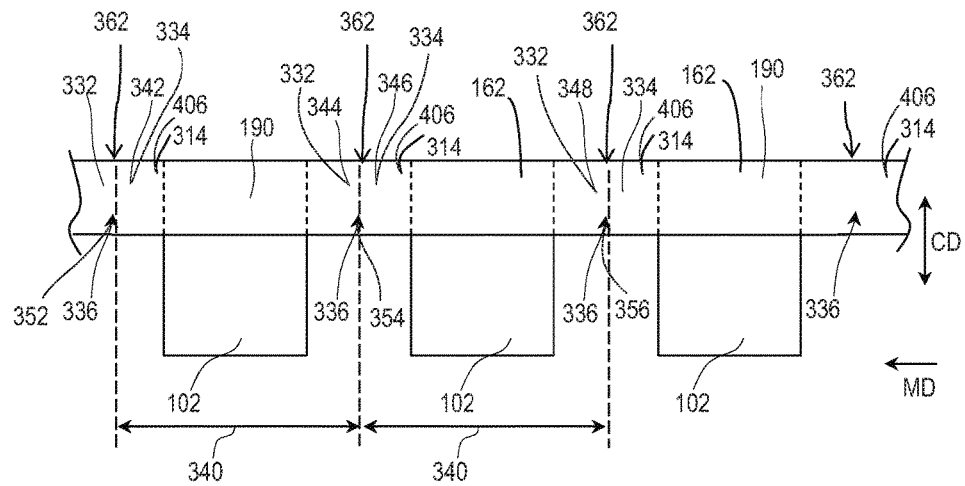
FIG. 7A is a top view of multiple discrete chassis attached to a first elastic belt substrate and a second elastic belt substrate in accordance with one non-limiting embodiment of the present disclosure.
Figure 7B:
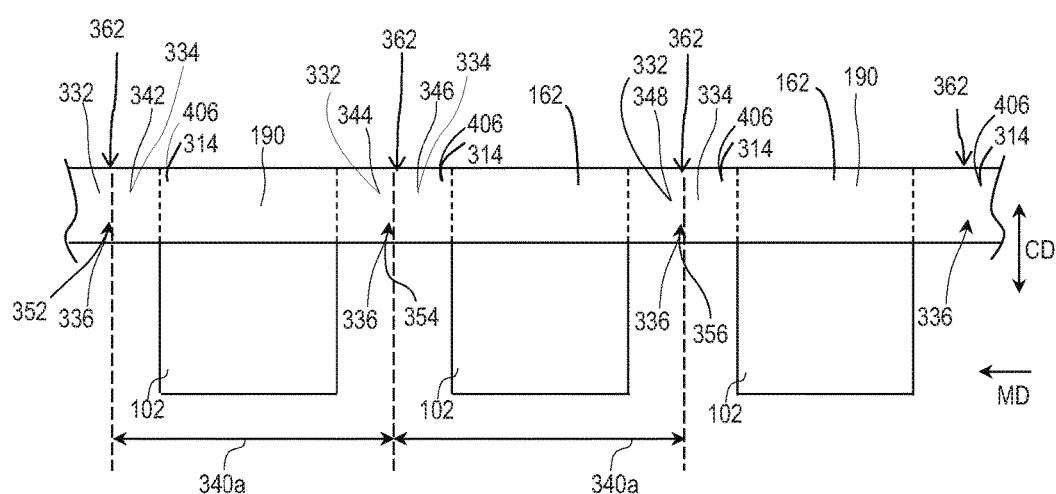
FIG. 7B is a top view of multiple discrete chassis attached to a first elastic belt substrate and a second elastic belt substrate in accordance with one non-limiting embodiment of the present disclosure.

Referring to FIGS. 7, 7A, and 7B, the substrate assembly 190 with the folded chassis 102 may advance in the machine direction MD to the bonder apparatus 200. As previously discussed, a substrate assembly 190 may include a first substrate and a second substrate in a facing relationship. It is to be appreciated that a substrate assembly 190 may include any number of substrates in any partially overlapping configuration. As previously described, the first substrate and the second substrate may be used to form a first elastic belt and a second elastic belt of the absorbent article. Thus, the first substrate and the second substrate may be elastically extensible in at least one of the machine direction MD and the cross direction. The first and second substrates may include regions 336 intermittently spaced along the machine direction, wherein each region 336 may include a leading portion 332 and a trailing portion 334. For example, as illustrated in FIG. 7A, a first region 352 may include a first leading portion 334 and a subsequent or adjacent region in the machine direction MD, such as a second region 354, may include a first trailing portion 344 and a second leading portion 346 and yet another subsequent or adjacent region in the machine direction MD, such as a third region 356, may include a second trailing portion 348.

Each leading portion and trailing portion may define a process product pitch 340, 340a. More specifically, for example, a process product pitch 340, 340a refers to the distance in the machine direction MD between the area at which a leading edge portion and a trailing edge portion meet in a first region to the area at which a leading edge portion and a second trailing edge portion in a subsequent, adjacent region meet, as illustrated in FIGS. 7A and 7B. The process product pitch may change based on the amount of elasticity of the substrate assembly and the process tension placed on the substrate assembly as it is advanced in the machine direction MD. It is to be appreciated that the process product pitch includes the process tension placed on the substrate during processing.

As illustrated in FIG. 7, the substrate assembly 190 may advance in the machine direction MD toward the bonder apparatus 200 at a first velocity $V_1$. Further, the substrate assembly 190 may be held at a process tension as the substrate assembly is advanced toward the bonder apparatus 200. In some embodiments, a guide roll 232 configured to rotate about an axis of rotation 234 and including an outer circumferential surface 236 may be used to transfer the substrate assembly 190 onto the bonding apparatus 200. The substrate assembly 190 may be disposed on a portion of the outer circumferential surface 236 of the guide roll 232 as the substrate assembly is transferred to the bonder apparatus 200.

As previously discussed, the bonder apparatus 200 includes one or more members 204 that may be configured to rotate about an axis of rotation 206 in a direction indicated by arrow 238. Each member 204 may be adjacent to a receiving surface 216. The receiving surface 216 may receive a region 336 of the substrate assembly 190. More specifically, the first member 204 may rotate about the axis of rotation 206 such that when the first member 204 reaches the guide roll 232 or, stated another way, the position where the substrate assembly 190 may be transferred to the bonder apparatus 200, the first member 204 is rotating about the axis of rotation 206 at the same velocity as the substrate assembly 190, which is the first velocity $V_1$. The first leading portion 342 may be disposed on the receiving surface 216 of the first member 204 as the first member 204 rotates at the first velocity past the guide roll 232. The first member 204 may continue to rotate about the axis of rotation 206 at the first velocity $V_1$ in the direction indicated by arrow 238.

In some embodiments, as previously discussed, the receiving surface 216 may include one or more apertures 218. The one or more apertures may be configured to transfer fluid, such as air, through the one or more apertures 218 in a direction toward the axis of rotation 206 causing the substrate assembly 190 to be secured to the receiving surface 216. It is to be appreciated that a mechanical device may be used to secure the substrate assembly 190 to the receiving surface 216. For example, the bonder apparatus 200 may include a clamping device. Further, a position control apparatus oriented adjacent to the bonder apparatus may be used to secure the substrate assembly 190. It is also to be appreciated that in some embodiments the substrate may not need to be held to the receiving surface 216 with a vacuum force or any other mechanical device.

A second member 210 may also rotate about the axis of rotation 206 in the direction indicated by arrow 238. The second member 210 may at least one of accelerate and decelerate such that the second member 210 is in position to receive the subsequent region 336 of the substrate assembly

190. Similar to above, the second member 210 may rotate about the axis of rotation 206 such that when the first member 204 reaches the guide roll 232 or, stated another way, the position where the substrate assembly 190 may be transferred to the bonder apparatus 200, the second member 210 is rotating about the axis of rotation 206 at the same velocity as the substrate assembly 190, which is the first velocity $V_1$. The first trailing portion 344 and the second leading portion 346 of the substrate assembly 190 may be disposed on the receiving surface 216 of the second member 210 as the second member 210 rotates at the first velocity past the guide roll 232. The second member 210 continues to rotate about the axis of rotation 206 at the first velocity.

Similar to the above, the one or more apertures 218 disposed on the receiving surface 216 may transfer fluid, such as air, through the one or more apertures 218 in a direction toward the axis of rotation 206 causing the substrate assembly 190 to be secured to the receiving surface 216. It is to be appreciated that a mechanical device may be used to secure the substrate assembly 190 to the receiving surface 216. For example, the bonder apparatus 200 may include a clamping device. Further, a position control apparatus oriented adjacent to the bonder apparatus may be used to secure the substrate assembly 190. It is also to be appreciated that in some embodiments the substrate may not need to be held to the receiving surface 216 with a vacuum force or any other mechanical device.

Additionally, the portion of the substrate assembly 190 between each of the adjacent regions 336 may be disposed on the support surface 202. In some embodiments, the product arc length 240, which is the distance measured along the support surface, or along the projected, circumferential path of the support surface, between a first leading portion and a first trailing portion, may be substantially equal to the process product pitch 340, 340*a*. Thus, as the substrate assembly 190 is transferred onto each member and rotates about the axis of rotation 206, the substrate assembly 190 may maintain the same process tension while disposed on the bonder apparatus 200 as the process tension of the substrate assembly 190 while being advanced toward the bonder apparatus 200. Similar to the above, it is to be appreciated that, in some embodiments, a third member may rotate about the axis of rotation 206 to receive the second trailing portion 348.

In summary, when a portion of the substrate assembly is disposed on the member, the member rotates about the axis of rotation at a first velocity, or the velocity at which the substrate assembly was advanced toward the bonder apparatus. Additionally, the substrate assembly maintains at least one of the product tension and the process product pitch as the substrate assembly is rotated about the axis of rotation by the members.

The regions 336 disposed on each of the receiving surfaces may undergo one or more process, such as bonding, cutting, or scoring, while rotating about the axis of rotation 206 at the first velocity $V_1$. After one or more processes are complete, each member 204 may rotate to a position adjacent to a second guide roll 246 or, stated another way, to a position at which the substrate assembly 190 may be removed from the member. The second guide roll 246 may be configured to rotate about an axis of rotation 248 and includes an outer circumferential surface 250. The substrate assembly 190 may be transferred from the receiving surface 216 and/or the support surface 202 to the outer circumferential surface 250 of the second guide roll 246. Pressure may be used to aid in the transfer of the substrate assembly 190. More specifically, as previously discussed, the one or more apertures 218 disposed on the receiving surface 216 may supply fluid, such as air, through the one or more apertures 218 in a direction away from the axis of rotation 206 causing the substrate assembly 190 to be removed from the receiving surface 216 and transferred to the outer circumferential surface 250 of the second guide roll 246. Upon removal from the bonder apparatus, the substrate assembly 190 continues to advance in the machine direction MD at the first velocity $V_1$.

Still referring to FIG. 7, the bonder apparatus 200 may include a process zone 242 and a repitch zone 244. The process zone 242 refers to the zone wherein the substrate assembly 190 is disposed on a member 204 and/or the support surface 202. As illustrated in FIG. 7, the process zone 242 may be from the position at which the substrate assembly 190 is transferred on to the bonder apparatus 200 to the position at which the substrate assembly 190 is removed from the bonder apparatus 200. The repitch zone 244 refers to the zone wherein there is no substrate assembly disposed on a member 204 and/or support surface 202. Stated another way, the repitch zone 244 may be from the position at which the substrate assembly 190 is removed from the bonder apparatus 200 to the position just before the substrate assembly 190 is transferred onto the bonder apparatus 200.

Each member 204 rotating within the process zone 242 rotates at substantially the same velocity as the substrate assembly 190 advancing in the machine direction MD toward the bonder apparatus 200. As illustrated in FIG. 7, the substrate assembly 190 advances in the machine direction MD toward the bonder apparatus at a first velocity $V_1$. Thus, each member 204 rotates about the axis of rotation 206 at a first velocity $V_1$ in the process zone 242. Further, as previously stated, adjacent members 204 maintain the tension of the substrate assembly 190, or stated another way, the product arc length 240 may be substantially the same as the process product pitch 340, 340*a*. The substrate assembly 190 may undergo one or more processes while being rotated by the members 204 in the process zone 242, as will be discussed in more detail herein.

Absorbent articles come in a variety of sizes. For example, one absorbent article may include a larger chassis and a larger belt as compared to another absorbent article which may include a smaller chassis and a smaller belt, as illustrated in FIGS. 7B and 7A, respectively. Thus, the repitch zone 244 may be used such that the absorbent article including the larger chassis and the larger belt can be manufactured on substantially the same equipment as the absorbent article including the smaller chassis and the smaller belt. This prevents manufacturers from having to switch out equipment or to make large modifications to the equipment for manufacturing different sized articles, which is costly and time consuming. The repitch zone 244 may be used to reposition the member 204 so that adjacent members 204 are in the appropriate positions to receive the substrate assembly 190. More specifically, each member 204 positioned in the repitch zone 244 may accelerate and/or decelerate to reach the appropriate position and velocity prior to receiving a portion of the substrate assembly 190. The position refers to the member 204 receiving and transferring the substrate assembly 190 such that the process product pitch is substantially equal to the product arc length and/or the tension in the substrate assembly 190 remains substantially constant.

The support surface 202 may allow the angle between each member 204 to change. The support surface 202 may include a first support segment 222 and a second support segment 224, as illustrated in FIGS. 6 and 7. As previously discussed, the first support segment 222 and the second support segment 224 may operatively engage to allow the distance between the first member 208 and the second member 210 to increase and decrease. In one embodiment, each of the first support segment 222 and the second support segment 224 may include one or more protrusions 230. The protrusions 230 of the first support segment 222 may be configured to intermesh with the protrusions 230 of the second support segment 224, as illustrated in FIGS. 6 and 7. In some embodiments, the support surface 202 may include a collapsible surface, such as a surface including a tooth-like design, as shown in FIG. 8A. The folds in the collapsible surface compress as the angle between adjacent members decreases and expand as the angle between adjacent members increases. It is to be appreciated that each support segment may be any structure that is configured to create a variable arc length, which allows the distance between adjacent members to change.

As illustrated in FIGS. 7 and 8A, in the process zone 242, the first member 204, 208 may be separated from the second member 204, 210 by a product angle α. The product angle α may be determined by the tension in the substrate assembly 190 and the process product pitch 340, 340a of the substrate assembly 190. The product angle α may be maintained between adjacent members while the member 204 rotates through the process zone 242. Once the member 204 rotates into the repitch zone 244, the members may be separated by a repitch angle β. The repitch angle β may be less than, equal to, or greater than the product angle α.

Figure 8B:
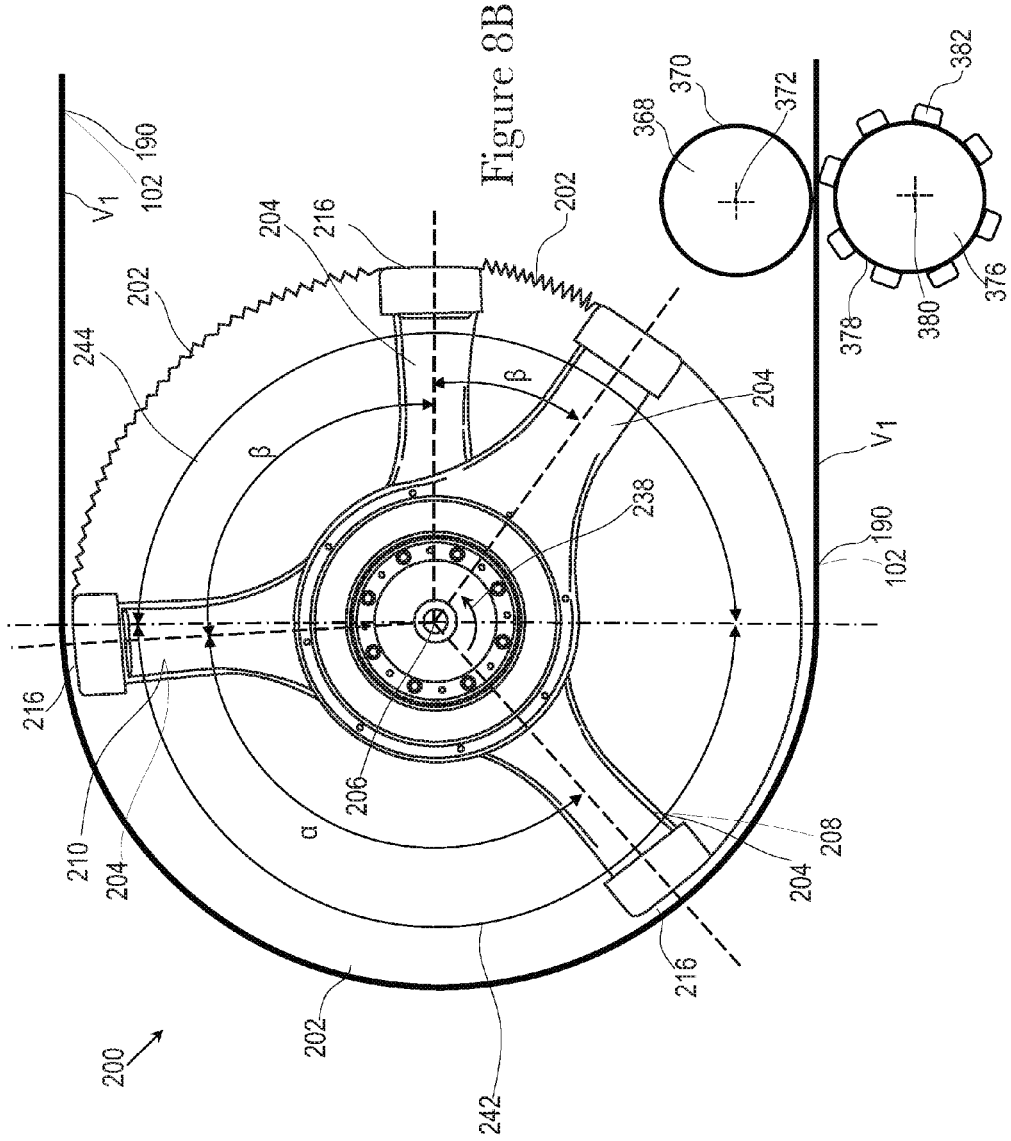
FIG. 8B is a side view of a bonder apparatus in accordance with one non-limiting embodiment of the present disclosure.

As illustrated in FIG. 8B, the bonder apparatus 200 may be positioned in any orientation about the axis of rotation 206. In some orientations, the substrate assembly 190 may be disposed on and/or removed from the bonder apparatus without the use of one or more guide rolls.

As previously discussed, the bonder apparatus 200 may include a process assembly 220. The process assembly 220 may be used to bond, cut, score, or perform some other action on the substrate assembly 190. In some embodiments, the process assembly 220 may be required to interact with additional apparatuses. For example, as illustrated in FIG. 7, the process assembly 220 may operatively engage an anvil roll 368 positioned adjacent the receiving surface 216 and/or the support surface 202. The anvil roll 368 includes an anvil roll outer circumferential surface 370 and may be adapted to rotate about an anvil roll axis of rotation 372. In some embodiments, the process assembly 220 may be used to act on the substrate assembly such that the substrate assembly may be required to undergo additional processes. For example, as illustrated in FIG. 8A, an anvil roll 368 including an anvil roll outer circumferential surface 370 may be used to operatively engage a bond roll 376. The bond roll 376 may be configured to rotate about an axis of rotation 380 and may include an outer circumferential surface 378. Further, one or more press members 382 may extend radially outward from the outer circumferential surface 378 of the bond roll 376. The substrate assembly 190 may be removed from the bonder apparatus and subsequently advanced through the bond roll 376 and the anvil roll 368. The press member 382 of the bond roll 376 may engage the outer circumferential surface 370 of the anvil roll 368 bonding a portion of the substrate assembly 190.

In some embodiments, the process assembly 220 may include a seaming station 548, such as disclosed in U.S. Pat. No. 8,778,127 and U.S. Patent Publication Nos. 2014/0110053 and 2014/0305593. The region 336 of the first and second belt substrates 406, 408, or the substrate assembly 190 may be positioned on the receiving surface 216 coincident with the seaming station 548. The seaming station 548 may be located radially inward from the receiving surface 216 and may be configured to bond a portion of the region 336 as the substrate assembly 190 is transferred by the bonder apparatus 200. Each seaming station 548 may include a fluid nozzle 578 and a press member 580, as illustrated in FIG. 9. As the member 204 rotates, fluid nozzles 578 of the seaming station 548 move radially outward toward the receiving surface 216. In addition, a fluid is heated to a temperature sufficient to at least partially melt at least a portion of the region 336 of the substrate assembly 190. The fluid nozzles direct a jet of the heated fluid onto at least a portion of the region 336 of the substrate assembly 190, which may include a first elastic substrate 406 and a second elastic substrate 408. The heated fluid partially melts at least a portion of the region 336. As the member 204 continues to rotate about the axis of rotation 206, the fluid nozzles retract radially inward from the receiving surface 216 and a press member 580 shifts radially outward toward the receiving surface 216. The press member then compresses the partially melted overlap area against the outer circumferential surface 370 of the anvil roll 368, creating one or more discrete bond sites 336a, as shown in FIG. 5E, between the first and second substrates. As the member 204 continues to rotate, the press member retracts radially inward from the receiving surface 216.

The press member 580 may be substantially rectangular in shape and defined by a press member top face, a press member bottom face, and a press member length. The press member 580 may include substantially square-shaped projections extending outwardly from the press member top face. The projections may be arranged into two or more rows. However, it is to be appreciated that the projections 423 may be regularly or irregularly spaced in various configurations and may be oriented in various directions. The projections 423 may have a circular, oval, or various other shapes. The projections 423 may have a height in the range of about 0.5 millimeters to about 5 millimeters. In some embodiments, the projections may have a width in the range of about 2 millimeters to about 10 millimeters, or between about 4 millimeters to about 6 millimeters.

It is also to be appreciated that the press member 386 may be discontinuous along the width of the press member 386 such that multiple segments of the press member 386 may define the press member length 387. In some embodiments, multiple segments of the press member may act independently to compress the region with different amounts of pressure. For example, each segment of the press member 386 may have an individual spring member, with each spring member designed to apply a different amount of force to different parts of the region. By applying different amounts of force in different locations, it may be possible to bond through different numbers of substrate layers or materials along the region. By selectively compressing portions with more or less force, portions of the substrates with fewer layers or different materials will not be over compressed and portions of the substrates with more layers or different materials will not be under compressed. In some embodiments, the press member may have more than one segment with each segment having different shaped projections, or may have different configurations of projections along the press member length.

Each heating apparatus 384 provides a pressurized fluid source for delivery of heated, pressurized fluid, such as air for example, to the fluid nozzle 578. In some embodiments, a valve may control egress of the fluid from the heating apparatus 384 and into a fluid nozzle 578. Each heating apparatus 384 is operatively connected to the press member 580.

The seaming station may also include a fluid nozzle 578. The fluid nozzle 578 may include one or more fluid orifices where the heated, pressurized fluid is released from the fluid nozzle 578. Each heating apparatus 384 may be immovably connected with a separate fluid nozzle 578. The fluid orifices 424 may be circular and may extend in a row along the fluid nozzle 578. Although, it is to be appreciated that the fluid orifices 424 may be arranged in various configurations. Also, it is to be appreciated that the fluid orifice may have an oval, square, or various other shapes. The fluid orifice 360 may have a diameter ranging from about 0.1 millimeters to about 6 millimeters.

The seaming station 548 may be positioned in a first configuration. In the first configuration, the fluid nozzles 578 are positioned radially outward near the receiving surface 216, while the press member 580 is positioned radially inward, away from the receiving surface 216. In addition, the fluid nozzles 578 are positioned at the same circumferential location as the projections 423 of the press member 386, such that the heated fluid is directed to the same locations on the region that will subsequently be compressed by the press member 580.

As the member 204 continues to rotate, the substrate assembly 204 and chassis 102 continues to be disposed on the receiving surface 216 and/or the support surface. At the same time, a jet of heated, pressurized fluid is directed from the heating apparatuses 384 out of the fluid nozzles 578 and onto the at least a portion of the region 336 of the first and second substrates 406, 408. The fluid nozzles 578 are maintained a preselected distance Y from the outer layer of the substrate to control the pressure applied to the region 336 by the heated fluid. In some embodiments, the distance Y between the outer layer of the substrate 406 and the fluid nozzles 578 may be maintained within 3 mm of the preselected distance Y. In some embodiments, the distance from the substrate assembly to the fluid nozzles may range from 0 millimeters to about 20 millimeters, or between about 0 millimeters and about 5 millimeters for example, or between about 0.5 millimeters and about 3 millimeters. Control of the distance between the first and second substrate and the fluid orifice may also result in a relatively more predictable fluid spray and melt pattern during the heating process.

A position control apparatus may be used to maintain the absorbent articles within a constant distance from the outer circumferential surface of the drum as the fluid is heating the region. In some embodiments, the position control apparatus 450 may be a belt apparatus 451 as shown in FIG. 8A. The position control apparatus 450 may be located adjacent the bonder apparatus 200 and may take the shape of at least a portion of the support surface 376 and/or the receiving surface 216. The position control apparatus may hold the substrate assembly 190 and/or the chassis 102 in the range of 0 millimeters to about 10 millimeters from the receiving surface 216, or between about 0.5 millimeters to about 5 millimeters from the receiving surface.

In some embodiments, the position control apparatus may be a mechanical apparatus such as clamps or another type of fastener that holds the region 336 of the substrate assembly 190 in place during the bonding process.

The seaming station 548 may also be positioned in a second configuration. In the second configuration, the press member 580 extends through the receiving surface 216, the heating apparatuses 384 are positioned radially inward, and the fluid nozzles 578 are located adjacent to the receiving surface 216. While the member 204 continues to rotate and the seaming station 548 is in the second configuration, the partially melted region 336 approaches the anvil roll 368 located adjacent the receiving surface 216. As the substrate assembly 190 passes between the anvil roll 368 and receiving surface 216, the press member 580, which is extended, compresses the partially melted region against the outer circumferential surface 370 of the anvil roll 368, as illustrated in FIG. 7.

The projections 423 of the press member 580 are configured to contact the same locations of the region that were at least partially melted by the heated fluid, thus forming discrete bond sites 336a in the region. A spring member may be used to apply a predetermined force to the region between the press member 580 and the anvil roll 368. Once compressed, the substrate assembly 190 and chassis 102 advance off of the receiving surface 216. The member continues to rotate and the seaming station shifts back to the first configuration in order to form discrete bond sites in a subsequent substrate assembly.

The heated fluid may include ambient air or other gases. It is to be appreciated that the fluid may be heated to various temperatures and pressurized to various pressures. For example, in some embodiments, the fluid may be heated up to a temperature ranging from the lower melting point of first and second substrates minus 30° C. to the lower melting point of the first and second substrates plus 100° C. In some embodiments, the fluid pressure may range from $0.1 \times 10^5$ Newtons per square meter to $1 \times 10^6$ Newtons per square meter. In some embodiments, the heated fluid may be directed toward at least one of the first and second substrates for a time interval ranging from 10 to 1000 milliseconds or greater. Shorter or greater time intervals may be used.

In some embodiments, the press member may compress the partially melted overlap area against the anvil roll outer circumferential surface at a pressure in the range of about $1 \times 10^5$ Newtons per square meter to about $1 \times 10^8$ Newtons per square meter. In some embodiments, the press member 366 may compress the first and second belt substrates for a time period ranging from 10 to 1000 milliseconds or greater. Shorter or greater time intervals may be used.

The temperature and pressure of the fluid are maintained within a specified range once the nominal set points are selected. For example, a set point may be selected and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected.

In some embodiments, the process assembly 220 may include a seaming station 548, such as disclosed in U.S. Patent Publication No. 2013/0218116. The seaming station 548 may use a heated fluid to bond at least a portion of the region 336 of the substrate assembly 190. The fluid may be sufficiently heated to enable at least a partial melting of at least a portion of the substrate assembly 190. A jet of the heated fluid may be directed toward the substrate assembly 190. The fluid may be allowed to penetrate the substrate assembly 190 such that at least a portion of each of the substrate layers are melted in the region, which may be an overlap area 362. The heated fluid, at a controlled temperature and pressure, may pass from the fluid outlet, leading to the formation of controlled and concentrated jets of heated fluid, which are directed toward the region 336 of the substrate assembly 190 to be joined.

By controlled, it is meant that the temperature and pressure are maintained within a specified range once the nominal set points are selected. For example, a set point may be selected from a range, and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected. For example, a nominal set point above the melting temperature of one or more of the materials to be joined may require a tighter control range than a nominal set point well below the melting temperature of one or more material to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The fluid may also be delivered with a pulsed application. The impact of the jet of heated fluid may be adjusted such that both the energy introduced by the jet plus the energy introduced by other means such as a heated anvil (if the anvil is heated), jet nozzle surface, deformation of the substrate, and the internal friction of substrate layers are sufficient to at least partially melt the meltable components in the region 336 to create a certain tackiness, which will form a strong bond in the region 336, which may include an overlap area 362, upon compression. The melting of the meltable components may occur in a non-uniform manner throughout substrates in the region 336.

The duration of energy transfer in the process described herein may be a dynamic process, and may create a temperature gradient across the cross sections of the meltable components. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be bonded have a softening point, the process may be adjusted to achieve a temperature in at least a portion of substrates between the softening point and the melting point. The use of a temperature at or above the softening point but below the melting point of one or more of the meltable components may allow for the creation of a strong bond between the substrate layers with reduced disruption to the structure of the meltable components e.g., attenuating or otherwise weakening the meltable components.

As discussed in more detail below, methods of joining at least two substrate portions may further comprise the step of compressing the region 336 of the substrate assembly 190 with the one or more pressure applying member while the meltable components are at least partially melted, and/or in the tacky state. The temperature of the pressure applying members may be at least below the melting point of the region 336. In some embodiments, the pressure applying member may be heated. The tackiness property of the meltable components permits the joining of substrate layers, which may include a first substrate 406 and a second substrate 408. The pressure applying members may be designed according to aesthetic criteria, for example, to provide discrete, shaped bonds where substrate layers are joined. Discrete bonds may also make the seam easier to open, if desired. The discrete bonds may generally take the shape and spacing of the pressure applying surfaces. As one example, the pressure applying members may be generally oval, or may have any other geometric or decorative shape consistent with the desired removal force and removal force perception. The pressure applying members may be regularly or irregularly spaced, and may be oriented in various directions.

The process assembly 220, as described with reference to FIGS. 7 and 8A, may be a seaming station 548. In some embodiments, the seaming station 548 may include a forming block 412 with a pressure applying member 414 extending outwardly from a face 416 of the forming block 412, as illustrated in FIG. 10A. While a single pressure applying member 414 is illustrated, there may be more than one pressure applying member. Adjacent and spaced laterally from the pressure applying member 64 is a fluid outlet 418 including a fluid orifice 420. The fluid outlet 418 may be in fluid communication with a fluid chamber 422 providing a pressurized fluid source for delivery of heated, pressurized fluid to the fluid outlet 418. A heating device 424 may be provided for heating the fluid within the fluid chamber 422. In some embodiments, a valve may control egress of fluid from the fluid chamber 422 and into the fluid outlet 418. As discussed above, a position control member may be used to maintain the substrate assembly 190 within a constant distance from the forming block as the fluid is heating the overlap area. The position control member may hold the substrates in the range of 0 millimeters to about 20 millimeters from the forming block, or between about 0.5 millimeters to about 5 millimeters from the forming block.

Still referring to FIG. 10A, the fluid outlet 418 may be arranged at an angle to vertical, such as for example between about 0 and about 75 degrees; between about 30 and 60 degrees; or about 45 degrees. As such, the fluid outlet 418 directs a jet 426 of heated fluid to a location at least partially beneath the pressure applying member 414 with a pressure applying surface 428 of the pressure applying member 414 spaced away from the substrate assembly 190.

A jet 426 of heated fluid (e.g., air) is directed toward the region 336 of the substrate assembly 190. The jet 426 of heated fluid may distribute in the machine direction MD and cross direction CD as it approaches the substrate assembly 190 forming substantially a cone shape such that the width W at the base of the jet 426 is greater than the diameter of the fluid orifice 420, as illustrated in FIG. 10C. While the jet 426 may be a cone shape, other spray patterns are possible, such as cylindrical, fan-shaped, etc., which may depend, at least in part, on the shape of the fluid orifice 420 and fluid outlet 418, the pressure of the fluid, and type of fluid being used.

The pressure applying member 414 and the fluid orifice 420 may also be separated from each other. For example, the fluid orifice 420 may be offset laterally from the pressure applying member 414. The fluid orifice 420 may be offset from the pressure applying member a distance such that the pressure applying member 414 does not intersect the jet 426. Additionally, the pressure applying surface 428 of the pressure applying member 414 may be spaced away from the substrate assembly 190 during the heating operation. Thus, the pressure applying member 414 does not interfere with the heating of the region 336 of the substrate assembly 190 by the jet 426 of heated fluid.

The forming block 62 may be moving at a constant speed, decreasing speed, increasing speed, or may be stationary while the jet 426 of heated fluid at least partially melts the substrate assembly 190. Once the substrate layers are at least partially melted, the member 204 may rotate the substrate assembly 190 to an anvil roll 368 and the forming block 412 may move toward the substrate assembly 190. Once the member 204 has reached the anvil roll 368, the pressure applying surface 428 of the pressure applying member 414 contacts the region 336 of the substrate assembly 190 at the at least partially melted area. The pressure applying member 414 compresses the region 336 of the substrate assembly 190 together between the pressure applying surface 428 and the anvil roll 368. It is to be appreciated that the anvil roll may alternatively be an anvil block, which traverses linearly to compress the region 336 of the substrate assembly 190.

FIG. 10B illustrates another embodiment of a seaming station 548 for bonding the substrate assembly 190. The traversing seaming apparatus 170 includes a forming block 412. The forming block 412 may include both pressure applying members 414 that extend outwardly from a face 416 of the heating and forming block 412 and fluid outlets 418 that are each in communication with a fluid chamber 422 providing a pressurized fluid source for delivery of heated, pressurized fluid to the fluid outlets 418. A heating device 424 may be provided for heating the fluid within the fluid chamber 422. In some embodiments, valves may control egress of fluid from the fluid chamber 422 and into the fluid outlets 418.

As above, jets of heated fluid are directed toward the substrate assembly 190 at the region 336, which may include an overlap area 362. The region 336 may be maintained a preselected distance from the fluid outlets 418, for example, using a position control device. Once the region 336 is at least partially melted, the forming block 412 may operatively engage the anvil roll 368 thereby compressing the region 336 of the substrate assembly 190.

Although some embodiments have been shown with a fluid outlet located away from and/or apart from the pressure applying member, it is to be appreciated that the fluid outlet may be configured so as to be combined with the pressure applying member. For example, FIG. 10C shows an embodiment with a combination fluid outlet 418 and pressure applying member 414. The pressure applying member 414 includes an outer wall extending outwardly from the face 416 of the forming block 412, an inner wall extending downwardly toward a fluid orifice 420 of the fluid outlet 418 and a pressure applying surface 428 extending between the outer wall and the inner wall.

Figure 11:
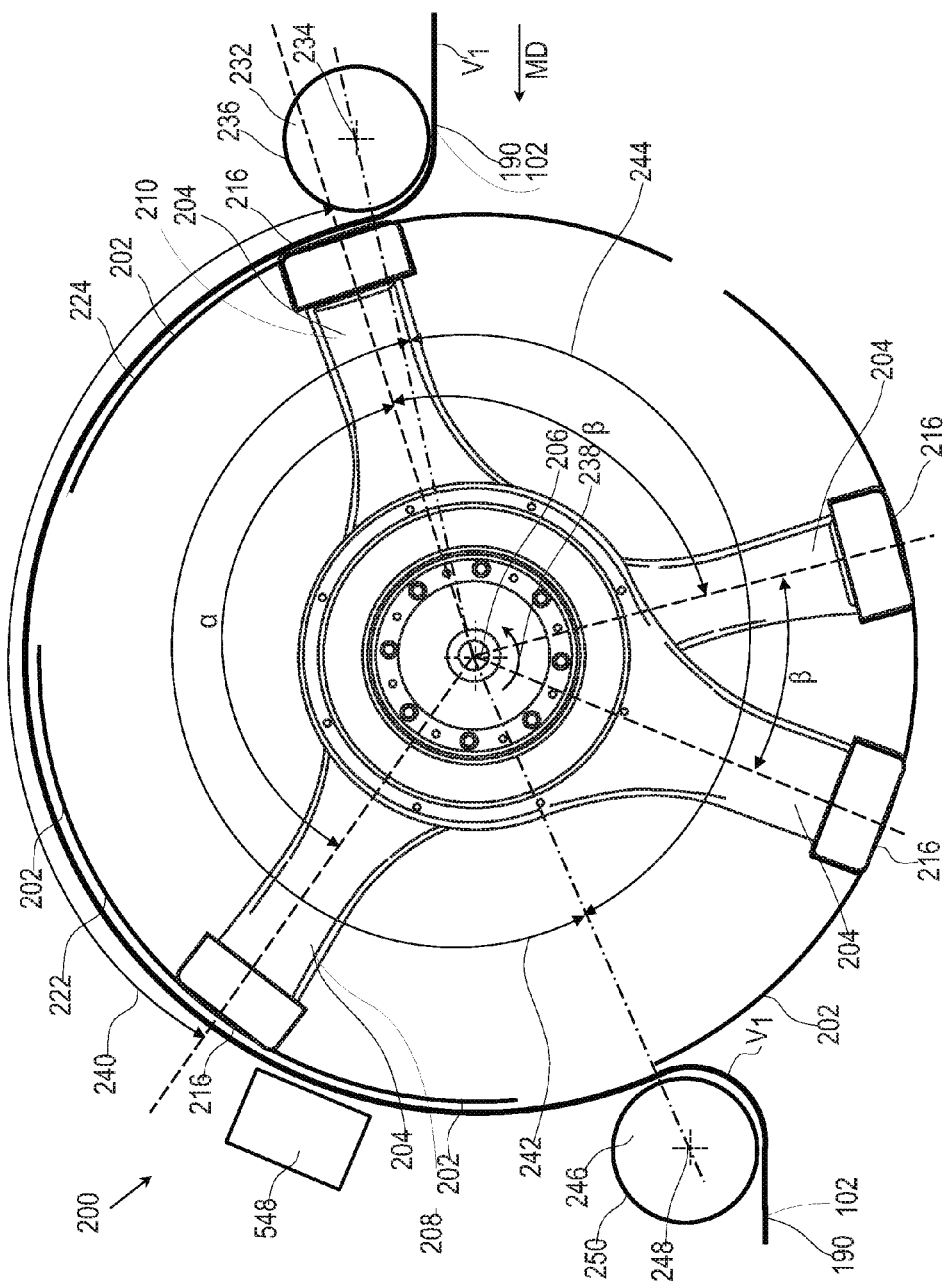
FIG. 11 is a side view of a bonder apparatus in accordance with one non-limiting embodiment of the present disclosure.

In some embodiments, the seaming station 548 may be external to the process assembly 220 and the process assembly may serve a different purpose, as illustrated in FIG. 11. For example, in some embodiments, the seaming station 548 may be positioned adjacent the receiving surface 216 and/or the support surface 202. It is also to be appreciated that in some embodiments, the process assembly 220 may include one of the aforementioned seaming stations 548 and an additional seaming station 548 may be positioned adjacent the receiving surface 216 and/or the support surface 202. In some embodiments, the process assembly 220 may include an anvil block that operatively engages the seaming station 548 positioned adjacent to the receiving surface 216.

Figure 12A:
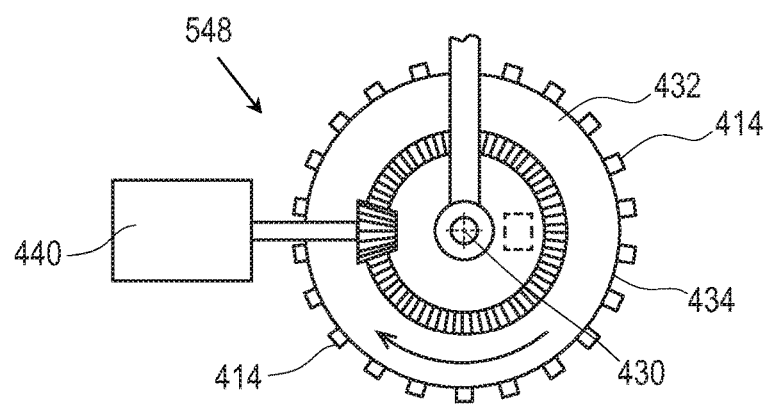
FIG. 12A is a side view of a seaming station in accordance with one non-limiting embodiment of the present disclosure.
Figure 12B:
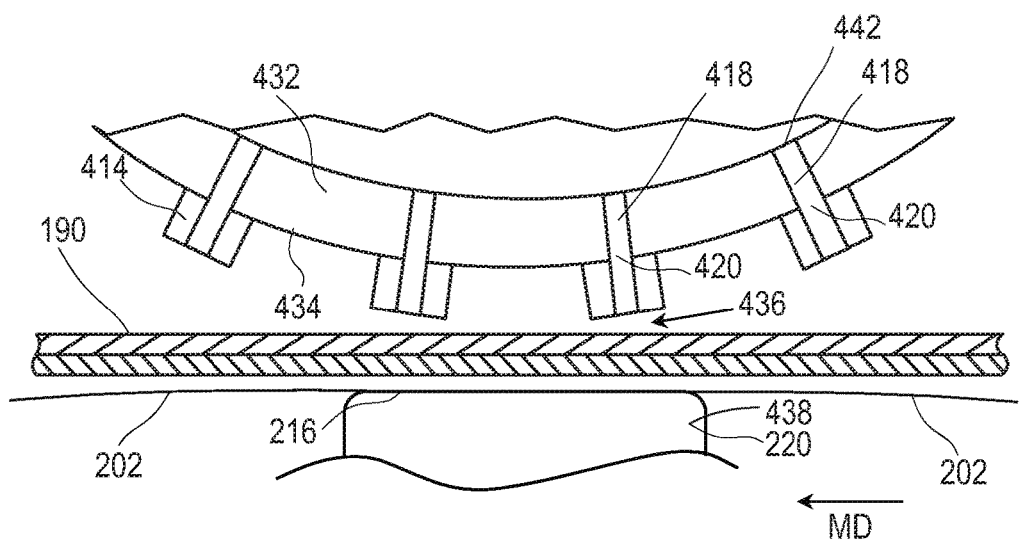
FIG. 12B is a partial side view of a seaming station in accordance with one non-limiting embodiment of the present disclosure.

In some embodiments, the seaming station 548 may be configured as illustrated in FIGS. 12A and 12B. The seaming station 548 may be configured to rotate about an axis of rotation 430 and to bond the region 336 of the substrate assembly 190. The rotary seaming station 548 may be driven by a drive member 440, which may be a motor. The rotary seaming station 548 may include a forming cylinder 432 with pressure applying members 414 extending radially outwardly from an outer circumferential surface 434 of the forming cylinder 432. It is to be appreciated that the forming cylinder 432 may include one or more pressure applying members 414. The pressure applying members 414 may include fluid outlets 418, each fluid outlet 418 may include a fluid orifice 420, as illustrated in FIG. 12B. The fluid outlet 418 may be in fluid communication with a fluid chamber providing a pressurized fluid source for delivery of heated, pressurized fluid, such as air for example, to the fluid outlet 418. In some embodiments, a heating device may be provided for heating the fluid within the fluid chamber. In some embodiments, a valve may control egress of fluid from the fluid chamber and into the fluid outlet 418.

As the member 204 and, more specifically, the receiving surface 216 disposed on the member 204 rotates to the seaming station 548, heated, pressurized fluid may be released from the fluid outlets 418 to heat the region 336 of the substrate assembly 190. The forming cylinder 432 continues to rotate during the release of fluid. The forming cylinder 432 may rotate at substantially the same speed as the member 204. A nip 436 may be formed between the forming cylinder 432 and the process assembly 220. More specifically, each pressure applying member 414 may operatively engage the receiving surface 216 of the process member 220, which may be an anvil block 438. The at least partially melted substrate assembly 190 may be advanced through the nip 436 between the forming cylinder 22 and an anvil block 438. The anvil block 438 may be positioned relative to the forming cylinder 432 such that a pressure applying surface 414 of the pressure applying member 414 may compress the region 336 of the substrate assembly 190, which may include an area of overlap 362, as the substrate assembly 190 advances through the nip 436. In some embodiments, the height of nip 436 may be adjusted to control the pressure applied to the region 336 of the substrate assembly 190. The pressure applied to at least a portion of the region 336 of the substrate assembly 190 may, for example, be in the range of $1 \times 10^5$ Newtons per square meter to $1 \times 10^8$ Newtons per square meter. Still referring to FIGS. 12A and 12B, the pressure applying member 414 may include, for example, a conical or cylindrical shaped fluid outlet 418 through which the heated fluid may be transferred to at least partially melt the meltable components of the substrate assembly 190. Although the following discussion refers to a cylindrical shaped fluid outlet 418, it is to be appreciated that fluid outlets 418 may have various other shapes, such as for example cones, boxes, and pyramids. A fluid jet nozzle may be connected to the fluid outlet 418. It is to be appreciated that the inlet 442 of the fluid outlet 418 and orifice 420 may be configured to have various different sizes. For example, in some embodiments, the diameter of inlet 442 the cylindrical shaped fluid outlet 418 may range from 1 millimeter to 8 millimeters and the diameter of orifice 420 of cylindrical shaped zone 34 may range from 0.1 millimeters to 6 millimeters.

As previously mentioned, the fluid may include ambient air or other gases. It is to be appreciated that the fluid may be heated to various temperatures and pressurized to various pressures. For example, in some embodiments, the fluid may be heated up to a temperature ranging from the lower melting point of the substrate layers of the substrate assembly 190 minus 30° C. to the lower melting point of the substrate layers of the substrate assembly 190 plus 100° C. In some example configurations, the fluid pressure may range from $0.1 \times 10^5$ Newtons per square meter to $1 \times 10^6$ Newtons per square meter.

In some embodiments, the heated fluid may be directed toward at least a portion of the region 336 of the substrate assembly 190 for a time interval ranging from 10 to 1000 milliseconds or greater. Shorter or greater time intervals may be used. It is to be appreciated that the pressure applying members 414 on the forming cylinder 432 may be disposed in a predetermined pattern, with each pressure applying member 2414 being configured to apply pressure or compress the region 336 of the substrate assembly 190 together after the region 336 have been at least partially melted by the heated fluid.

In addition, there may be a predetermined but adjustable relationship between the surface velocities of the forming cylinder 432 and the member 204. Such a relationship can be synchronous, or asynchronous, that is, with equal surface velocities or with a predetermined surface velocity differential with either the forming cylinder 432 or the member 204 being driven faster than the other.

Similar to the above, in some embodiments, the substrate assembly 190 may be maintained a preselected distance Y from the fluid orifice 420 as the fluid orifice releases the fluid. In some embodiments, the distance Y between the surface of the substrate assembly facing the forming cylinder 432 and the fluid orifice 420 may be between about 0 mm and about 20 mm, such as between about 0 mm and about 5 mm, such as between about 0.5 mm and about 3 mm. The distance Y may be maintained within 3 mm of the preselected distance Y. Control of the distance Y may also result in a relatively more predictable fluid spray and melt pattern during the heating process. The process assembly 202 may be an ultrasonic processes system, such as disclosed in European Patent Application No. 2796271A1.

In some embodiments, the process assembly 202 may act on the substrate assembly 190 in processes different than those previously disclosed. For example, the process assembly 202 may include a cutting mechanism, such as with a laser, a knife, or ultrasonic cutting device.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a bond, the method comprising the steps of:
   advancing a substrate assembly in a machine direction at a first velocity, wherein the substrate assembly comprises a process product pitch defined by a leading portion and a trailing portion, and wherein the substrate assembly comprises a first substrate in facing relationship with a second substrate;
   rotating a bonder apparatus about an axis of rotation, wherein the bonder apparatus comprises a support surface between each of a first member and a second member adjacent the first member, wherein each of the first and second member comprises a proximal end portion adjacent the axis of rotation and a distal end portion opposite the proximal end portion;
   rotating the first member about the axis of rotation at the first velocity, wherein the first member comprises a first receiving surface positioned at the distal end portion of the first member;
   receiving the leading portion on the first receiving surface of the first member, wherein the first member and the second member are separated by a repitch angle;
   at least one of accelerating and decelerating the second member such that the first member and the second member are separated by a product angle, wherein the second member comprises a second receiving surface positioned at the distal end portion of the second member;
   receiving the trailing portion on the second receiving surface of the second member and rotating the second member about the axis of rotation at the first velocity, wherein the leading portion and the trailing portion are separated by a product arc length, wherein the product arc length is substantially equal to the process product pitch;
   heating a fluid to a temperature sufficient to at least partially melt the first substrate and the second substrate;
   directing jets of the fluid toward the leading portion and the trailing portion to form a bond, wherein each of the first receiving surface and the second receiving surface define a fluid aperture, and wherein the jets of heated fluid pass through the fluid apertures toward the substrate assembly;
   partially melting at least a portion of at least one of the leading portion and the trailing portion; and
   compressing a portion of the substrate assembly.

2. The method of claim 1, wherein each of the first receiving surface and the second receiving surface define a vacuum aperture, and wherein a fluid passes through the vacuum aperture toward the axis of rotation.

3. The method of claim 1, further comprising the step of maintaining the position of the substrate assembly on the surface of the first and second members using a position control member.

4. The method of claim 1, wherein a jet of the heated fluid is expelled from a fluid nozzle.

5. The method of claim 4, further comprising the step of maintaining the fluid nozzle a distance Y from an outer surface of the substrate assembly.

6. The method of claim 5, wherein the distance Y from the fluid nozzle to the outer surface of the substrate assembly is in the range of about 0 to about 10 millimeters.

7. The method of claim 1, wherein a jet of the heated fluid is at a temperature ranging from a lower melting point of the first and second substrates minus 30° C. to the lower melting point of the first and second substrates plus 100° C.

8. The method of claim 1, wherein a jet of the heated fluid is directed at the first and second substrates at a pressure in the range of about $0.1 \times 10^5$ Newtons per square meter to about $1 \times 10^6$ Newtons per square meter.

9. The method of claim 1, wherein a jet of the heated fluid is directed at the first and second substrates between about 10 milliseconds and about 1000 milliseconds.

10. The method of claim 4, wherein the fluid nozzle includes a fluid orifice, and the fluid orifice is spaced from about 0.5 millimeters to about 5 millimeters apart from an aperture in the surface of at least one of the first member and the second member.

11. The method of claim 1, wherein the step of compressing the substrate assembly comprises advancing the substrate assembly between an anvil roll and a bond roll.

12. The method of claim 1, wherein the first substrate and the second substrate are nonwovens.

13. The method of claim 1, wherein the fluid is ambient air.

14. The method of claim 1, further comprising the step of cutting the substrate assembly into individual articles with a knife roll.

15. The method of claim 1, wherein the step of compressing the substrate assembly includes cutting the first and second substrates into individual articles.

16. The method of claim 1, further comprising the step of applying a vacuum to a portion of the leading portion and the trailing portion.

17. The method of claim 1, wherein the support surface comprises a first support segment and a second support segment, wherein each of the first support segment and the second support segment comprise a distal end portion and a proximal end portion opposite the distal end portion, and wherein the proximal end portion of the first support segment is joined to the first member and the proximal end portion of the second support segment is joined to the second member, and wherein the distal end portion of the first support segment is configured to operatively engage the distal end portion of the second support segment.

18. The method of claim 1, further comprising the steps of:
removing the substrate assembly from the first receiving member;
at least one of accelerating and decelerating the first member;
removing the substrate assembly from the second receiving member;
at least one of accelerating and decelerating the second member,
wherein the first receiving member is configured to receive a leading portion of the substrate assembly and the second receiving member is configured to receive a trailing portion of the substrate assembly, and wherein the first member and the second member are configured to rotate about the axis of rotation at a first velocity maintaining the process product pitch.

19. The method of claim 1, wherein the repitch angle is at least one of greater than or less than the product angle.

20. A method for forming a bond, the method comprising the steps of:
advancing a substrate assembly in a machine direction at a first velocity, wherein the substrate assembly comprises a process product pitch defined by a leading portion and a trailing portion;
rotating a bonder apparatus about an axis of rotation, wherein the bonder apparatus comprises a support surface between each of a first member and a second member adjacent the first member, wherein each of the first and second member comprises a proximal end portion adjacent the axis of rotation and a distal end portion opposite the proximal end portion, and wherein the bonder apparatus comprises a process zone and a repitch zone;
rotating the first member and the second member about the axis of rotation at the first velocity in the process zone, wherein the first member comprises a first receiving surface positioned at the distal end portion of the first member and the second member comprises a second receiving surface positioned at the distal end portion of the second member;
transferring the leading portion on the first receiving surface and transferring the trailing portion on the second receiving surface in the process zone, wherein the first receiving surface and the second receiving surface are positioned such that the leading portion and the trailing portion are separated by a product arc length;
heating a fluid to a temperature sufficient to at least partially melt a portion of the substrate assembly;
directing jets of the heated fluid toward the substrate assembly to form a bond, wherein each of the first receiving surface and the second receiving surface define a fluid aperture, and wherein the jets of heated fluid pass through the fluid apertures toward the substrate assembly;
partially melting a portion of the substrate assembly; and
at least one of accelerating and decelerating the first member and the second member in the repitch zone, wherein the substrate assembly is not disposed on the first receiving surface and the second receiving surface.

21. The method of claim 20, further comprising the step of compressing the substrate assembly.

22. The method of claim 21, wherein the step of compressing includes advancing the substrate assembly through a bond roll and an anvil roll, wherein the bond roll comprises a press member that extends radially outward from an outer circumferential surface of the bond roll.

23. The method of claim 22, wherein the anvil roll comprises an outer circumferential surface that rotates about an anvil axis of rotation, wherein the outer circumferential surface is configured to operatively engage the press member.

* * * * *